(12) United States Patent
Shirley

(10) Patent No.: US 10,935,364 B2
(45) Date of Patent: Mar. 2, 2021

(54) METHOD AND APPARATUS FOR REMOTE SENSING OF OBJECTS UTILIZING RADIATION SPECKLE

(71) Applicant: Lyle G. Shirley, Boxborough, MA (US)

(72) Inventor: Lyle G. Shirley, Boxborough, MA (US)

( * ) Notice: Subject to any disclaimer, the term of this patent is extended or adjusted under 35 U.S.C. 154(b) by 0 days.

(21) Appl. No.: 16/357,263

(22) Filed: Mar. 18, 2019

(65) Prior Publication Data

US 2020/0025552 A1 Jan. 23, 2020

Related U.S. Application Data

(60) Continuation of application No. 15/420,555, filed on Jan. 31, 2017, now Pat. No. 10,281,257, which is a
(Continued)

(51) Int. Cl.
*G01B 11/02* (2006.01)
*G01B 9/02* (2006.01)
(Continued)

(52) U.S. Cl.
CPC ......... *G01B 9/02094* (2013.01); *A61B 5/117* (2013.01); *G01B 9/02004* (2013.01);
(Continued)

(58) Field of Classification Search
CPC ............ G01B 9/02094; G01B 9/02096; G01B 9/02004; G01B 9/02005; G01B 9/02069;
(Continued)

(56) References Cited

U.S. PATENT DOCUMENTS 4,018,531 A * 4/1977 Leendertz ............... G01H 9/002
356/512
4,352,565 A * 10/1982 Rowe ................. G01B 9/02094
356/502
(Continued)

OTHER PUBLICATIONS

Nonconventional 3D imaging using wavelength-dependent speckle, Shirley et al, The Lincoln Laboratory Journal, vol. 9, No. 2, 1996 (Year: 1996).*
(Continued)

*Primary Examiner* — Kara E. Geisel
*Assistant Examiner* — Jonathon Cook
(74) *Attorney, Agent, or Firm* — John Brooks Law LLC; John J. Brooks, III

(57) ABSTRACT

Disclosed are systems and methods to extract information about the size and shape of an object by observing variations of the radiation pattern caused by illuminating the object with coherent radiation sources and changing the wavelengths of the source. Sensing and image-reconstruction systems and methods are described for recovering the image of an object utilizing projected and transparent reference points and radiation sources such as tunable lasers. Sensing and image-reconstruction systems and methods are also described for rapid sensing of such radiation patterns. A computational system and method is also described for sensing and reconstructing the image from its autocorrelation. This computational approach uses the fact that the autocorrelation is the weighted sum of shifted copies of an image, where the shifts are obtained by sequentially placing each individual scattering cell of the object at the origin of the autocorrelation space.

20 Claims, 10 Drawing Sheets

Related U.S. Application Data continuation of application No. 14/281,255, filed on May 19, 2014, now Pat. No. 9,582,883, which is a continuation-in-part of application No. 13/568,229, filed on Aug. 7, 2012, now Pat. No. 8,761,494, which is a division of application No. 11/764,196, filed on Jun. 16, 2007, now Pat. No. 8,265,375, said application No. 14/281,255 is a continuation-in-part of application No. 13/189,349, filed on Jul. 22, 2011, now Pat. No. 8,736,847, and a continuation-in-part of application No. 12/921,185, filed as application No. PCT/US2009/037999 on Mar. 23, 2009, now Pat. No. 8,810,800.

(60) Provisional application No. 60/814,149, filed on Jun. 16, 2006, provisional application No. 60/816,305, filed on Jun. 23, 2006, provisional application No. 60/816,982, filed on Jun. 27, 2006, provisional application No. 61/367,409, filed on Jul. 24, 2010, provisional application No. 61/435,283, filed on Jan. 22, 2011, provisional application No. 61/070,352, filed on Mar. 22, 2008, provisional application No. 61/115,923, filed on Nov. 18, 2008.

(51) Int. Cl.
| | | |
|---|---|---|
| *A61B 5/117* | (2016.01) | |
| *G06F 21/32* | (2013.01) | |
| *G06K 9/20* | (2006.01) | |
| *G06K 9/62* | (2006.01) | |
| *G06T 7/55* | (2017.01) | |
| *G01B 11/24* | (2006.01) | |
| *G06T 7/521* | (2017.01) | |
| *G01B 11/14* | (2006.01) | |
| *A61B 5/00* | (2006.01) | |

(52) U.S. Cl.
CPC ..... *G01B 9/02005* (2013.01); *G01B 9/02069* (2013.01); *G01B 9/02083* (2013.01); *G01B 9/02096* (2013.01); *G01B 11/14* (2013.01); *G01B 11/2441* (2013.01); *G06F 21/32* (2013.01); *G06K 9/2018* (2013.01); *G06K 9/629* (2013.01); *G06T 7/521* (2017.01); *G06T 7/55* (2017.01); *A61B 5/0077* (2013.01); *A61B 2576/00* (2013.01); *G06T 2207/10152* (2013.01)

(58) Field of Classification Search
CPC ............ G01B 9/02083; G01B 9/02017; G01B 9/02019; G01B 11/14; G01B 11/2441; G06T 7/55; G06T 7/521; G06T 2207/10152; G06F 21/32; G06K 9/2018; G06K 9/629

See application file for complete search history.

(56) References Cited

U.S. PATENT DOCUMENTS

| | | | | |
|---|---|---|---|---|
| 5,627,363 | A * | 5/1997 | Paxman | G01B 11/24 250/208.1 |
| 6,188,482 | B1 * | 2/2001 | Cloud | G01B 9/0201 356/491 |
| 6,525,824 | B1 * | 2/2003 | Gutierrez | G01B 9/02019 356/495 |
| 2003/0179382 | A1 * | 9/2003 | Peterson, Jr. | G01B 11/162 356/502 |

OTHER PUBLICATIONS

Liang, Wei (2008) Study of Optical Phase Lock Loops and the Applications in Coherent Beam Combining and Coherence Cloning. Dissertation (Ph.D.), May 2008, California Institute of Technology, pp. 55-77, doi:10.79071YHBF-KW11. https://resolver.caltech.edu/CaltechETD:etd-03272008-143400, 23 pgs.

Paschotta, Rudiger, Coherent Beam Combining, Printed from https://www.rp-photonics.com/coherent_beam_combining.html, as retrieved on Jul. 30, 2020, 6 pgs.

* cited by examiner

FIG. 4a
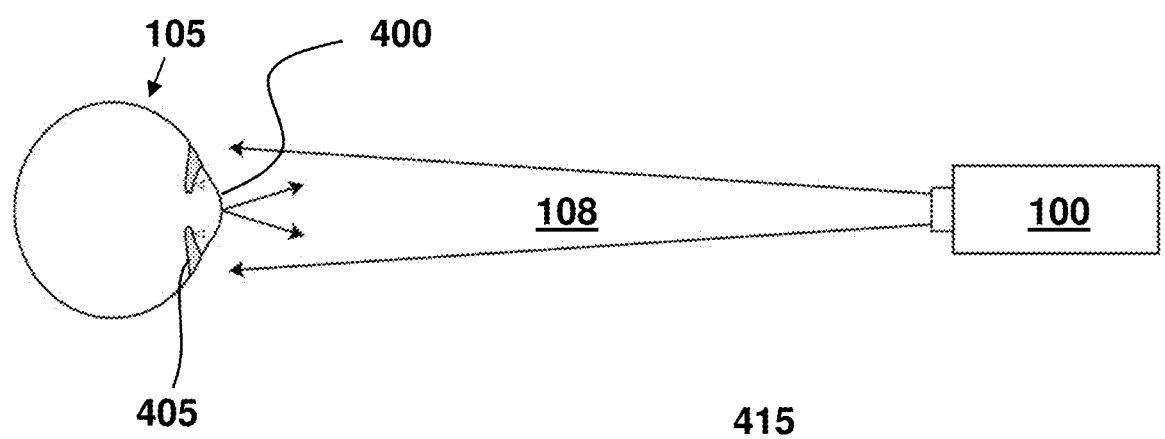
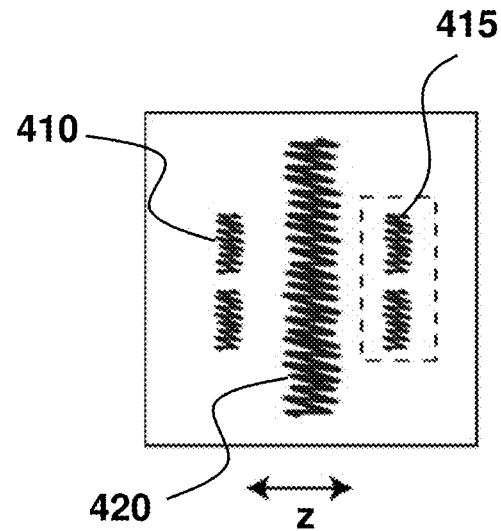
FIG. 4b

METHOD AND APPARATUS FOR REMOTE SENSING OF OBJECTS UTILIZING RADIATION SPECKLE

CROSS-REFERENCE TO RELATED APPLICATIONS

This application is a Continuation application of U.S. patent application Ser. No. 15/420,555 filed on Jan. 31, 2017; U.S. patent application Ser. No. 15/420,555 is a Continuation application of U.S. patent application Ser. No. 14/281,255 filed on May 19, 2014 now U.S. Pat. No. 9,582,883 issued Feb. 28, 2017; U.S. patent application Ser. No. 14/281,255 is a Continuation-in-Part of U.S. patent application Ser. No. 13/568,229 filed on Aug. 7, 2012 now U.S. Pat. No. 8,761,494 issued Jun. 24, 2014; U.S. patent application Ser. No. 13/568,229 is a Divisional application of U.S. patent application Ser. No. 11/764,196 filed on Jun. 16, 2007, now U.S. Pat. No. 8,265,375 issued Sep. 11, 2012; U.S. patent application Ser. No. 11/764,196 claims the benefit of U.S. Pat. App. No. 60/814,149 filed on Jun. 16, 2006, U.S. Pat. App. No. 60/816,305 filed on Jun. 23, 2006 and U.S. Pat. App. No. 60/816,982 filed on Jun. 27, 2006; U.S. patent application Ser. No. 14/281,255 is also a Continuation-in-Part application of U.S. patent application Ser. No. 13/189,349 filed on Jul. 22, 2011 now U.S. Pat. No. 8,736,847 issued May 27, 2014; U.S. patent application Ser. No. 13/189,349 claims benefit of U.S. Pat. App. No. 61/367,409 filed Jul. 24, 2010 and U.S. Pat. App. No. 61/435,283 filed on Jan. 22, 2011; U.S. patent application Ser. No. 14/281,255 is also a Continuation-in-Part application of U.S. patent application Ser. No. 12/921,185 having a 371(c) date of Sep. 7, 2010 now U.S. Pat. No. 8,810,800 issued Aug. 19, 2014; U.S. patent application Ser. No. 12/921,185 is a 371 of PCT App. No. PCT/US09/37,999 filed Mar. 23, 2009; PCT App. No. PCT/US09/37,999 claims benefit of U.S. Pat. App. No. 61/070,352 filed Mar. 22, 2008 and U.S. Pat. App. No. 61/115,923 filed on Nov. 18, 2008; and all of said applications are herein incorporated by reference in their entirety.

STATEMENT REGARDING FEDERALLY SPONSORED RESEARCH OR DEVELOPMENT

This invention was made with Government support under Contract # FA8721-05-C-0002 awarded by the United States Air Force. The Government has certain rights in the invention.

REFERENCE TO SEQUENCE LISTING, A TABLE, OR A COMPUTER PROGRAM LISTING COMPACT DISC APPENDIX

Not Applicable

BACKGROUND OF THE INVENTION

1. Field of the Invention

This invention involves the application of tunable radiation sources to remotely sense objects with opaque surfaces. More specifically, this invention addresses the systems and methods to extract information about the object by observing variations of the radiation pattern caused by illuminating the object with coherent radiation sources and changing the outputting of wavelengths of the source.

2. Description of the Prior Art

Multiple technologies and methods are used to sense and construct multi-dimensional representations of remote objects. Common three-dimensional imaging solutions include triangulation-based laser scanners, scanning modulated waveform laser radars and imaging time-of-flight laser radars. However, each of these technologies has limitations.

Triangulation-based laser scanners direct a laser beam at the surface from one end of the scanner and receive the reflected laser light at the other end of the scanner. By measuring the angle, the distance can be calculated. Although capable of high accuracy, they are of limited use for long range scanners, because the longer the range, the larger the scanner needs to be. Shadowing effects also impact the ability of this technique to construct accurate representations of objects.

Scanning modulated waveform laser radars modulate a laser beam in a known way and record the returning beam. By comparing the outgoing and incoming waveforms, the distance can be computed. This technique is a relatively slow point-by-point measurement technique requiring the beam to scan the object. This technique provides limited resolution.

Imaging time-of-flight laser radars direct a laser beam out towards the object, then measure how long it takes for the light to return. By using the time taken for the response and the speed of light, the distance can be calculated. Although time-of-flight solutions are capable of operating over very long distances, due to the high velocity of light, timing the round-trip time is difficult and the accuracy of the range resolution is relatively low.

It is also known that "speckle" can be used to obtain three-dimensional information about a remote object. "Speckle" is an interference phenomenon that occurs when coherent radiation (e.g., laser light) is reflected from a rough or multiply scattering sample onto a detection plane. Due to scattering of photons from and within the sample, different photons travel different distances to the detection plane. As a result, the light reflected or backscattered from the sample, if temporally coherent, interferes at the detection plane, producing a grainy pattern known as "speckle." Techniques exist to utilize speckle patterns, called speckle-pattern sampling, to obtain range information from the wavelength of speckle as well as measure the spatial dependence of the speckle pattern to resolve the object laterally. These speckle patterns can be detected with a sensor array at each of a set of equally spaced laser frequencies. The individual frames are stacked to form a three-dimensional data array, and a three-dimensional Fourier Transform (FT) is performed on this data array. The FT process yields the three-dimensional autocorrelation function of the three-dimensional image of the object. The use of "speckle" for three-dimensional imaging is a technique disclosed in U.S. Pat. No. 5,627,363 which is herein incorporated by reference in its entirety. Techniques for speckle-pattern sampling are also described in L. Shirley and G. Hallerman, "Technical Report 1025, "Application of Tunable Lasers to Laser Radar and 3D Imaging," MIT Lincoln Lab Technical Report 1025, 26 Feb. 1996, which is herein incorporated by reference in its entirety.

Although speckle-pattern sampling is an improvement in the art of three-dimensional imaging, there are still shortcomings to this technique. With speckle-pattern sampling, reference points and reference planes can be used to produce the three-dimensional image from the autocorrelation of an image. However, it is not always possible to implement the reference-point techniques that currently exist in the art. There are situations where the imaging system may not be able to predetermine or place a reference point in proximity of the object. There are also situations where significant benefits can be gained from a movable and self contained imaging system that can create reference points.

Where reference points are not possible, and phase information of the received light is not known, speckle-pattern sampling requires demanding computational approaches for reconstructing the three-dimensional image from its autocorrelation. It has been an ongoing challenge to determine methods and systems to efficiently transform this autocorrelation data into a representation of an object.

Therefore, there exists a need in the art for three-dimensional imaging systems and methods that addresses these shortcomings.

BRIEF SUMMARY OF THE INVENTION

It is an object of this invention to provide systems and methods to extract information about the size and shape of an object by observing variations of the radiation pattern caused by illuminating the object with coherent radiation sources and changing the wavelengths of the source.

It is an object of the invention to provide imaging systems comprising a source of coherent radiation outputting a plurality of wavelengths illuminating an object creating a plurality of speckle patterns each corresponding to the plurality of wavelengths, at least one sensor at a location relative to the object to determine the intensity of the speckle pattern for each of the plurality of wavelengths, a processor receiving information from the sensor, the processor having means for constructing at least one autocorrelation of the object from the intensities of the speckle patterns, a controller for controlling the source of coherent radiation creating a focused laser beam for use as a projected reference point and the processor further comprising means for executing a regional image selection technique to construct a representation of the object utilizing the projected reference point and the autocorrelation.

It is another object of this invention to provide an imaging apparatus comprising a source of coherent radiation outputting a plurality of wavelengths illuminating an object creating a plurality of speckle patterns each corresponding to the plurality of wavelengths, at least one sensor at a location relative to the object to determine the intensity of the speckle pattern for each of the plurality of wavelengths, a processor receiving information from at least one sensor, the processor having means for constructing one or more autocorrelations of the object from the intensities of the speckle pattern, the processor having means for receiving one or more speckle patterns influenced by a reference point created by an area of a curved surface and the processor further comprising means for executing a regional image selection technique to construct a representation of the object utilizing the projected reference point and the autocorrelation.

It is another object of the invention to provide an imaging apparatus comprising a source of coherent radiation outputting a plurality of wavelengths illuminating an object creating a plurality of speckle patterns each corresponding to the plurality of wavelengths, at least one sensor at a location relative to the object to determine the intensity of the speckle pattern for each of the plurality of wavelengths, a processor receiving information from at least one sensor, a processor having means for constructing one or more autocorrelations of the object from the intensities of the speckle pattern, and the processor further comprising means to compare at least one of the autocorrelations.

It is another object of the invention to provide a method to construct a representation of an object from speckle patterns comprising the steps of shifting and comparing autocorrelation points of an autocorrelation where the autocorrelation comprises autocorrelation points that lie on a copy, the copy comprising autocorrelation points representing an object and autocorrelation points that do not lie on the copy and eliminating autocorrelation points that do not lie on the copy, constructing a representation of the object from the autocorrelation points that lie on the copy.

It is another object of the invention to provide a method to construct a representation of an object wherein the method of shifting and comparing described above further comprises the steps of selecting one or more shift candidates comprising autocorrelation points that lie on the copy, shifting the autocorrelation to the shift candidates creating a shifted autocorrelation, comparing the shifted autocorrelation with the autocorrelation and eliminating autocorrelation points that do not lie on the copy, creating a partial reconstruction of the copy, updating the partial reconstruction of the copy with steps further comprising: selecting one or more additional shifts, shifting the autocorrelation to said additional shifts, creating a second shifted autocorrelation and comparing the second shifted autocorrelation with the partial reconstruction of the copy, and eliminating autocorrelation points that do not lie on the copy, creating an update to the partial reconstruction of the copy; repeating the foregoing steps to update the partial reconstruction of the copy until the partial reconstruction of the copy comprises a representation of the object and outputting the representation of the object.

It is another object of the invention to provide an imaging apparatus comprising a source of coherent radiation rapidly outputting a plurality of wavelengths illuminating an object creating a plurality of speckle patterns each corresponding to the plurality of wavelengths, a sensor at a location relative to the object to determine the intensity of the speckle pattern for each of the plurality of wavelengths, means to associate the outputting of each of the plurality of wavelengths from the radiation source with the receipt of corresponding intensities of the speckle pattern for each of the plurality of wavelengths at the sensor and a processor receiving information from the sensor, and processor having means for constructing one or more autocorrelations of the object from the intensities of the speckle patterns.

It is an object of the invention to provide high lateral resolution of images without the need for large precision optics. In this invention, resolution can be determined by a sensor array size It is a further object of this invention to provide enhanced range resolution of images through tuning the wavelength of coherent radiation sources. In this invention, range resolution can be determined by the tuning bandwidth.

It is another object of this invention to provide an imaging solution that has reduced sensitivity to atmospheric turbulence. This invention is insensitive to turbulence at or near the sensor plane.

It is an object of this invention to provide an imaging solution that has reduced laser coherence requirements. In this invention, phase coherence is not necessary between laser frequency steps.

It is a further object of this invention to provide an imaging solution that has reduced sensor bandwidth requirements.

It is another object of this invention to provide an imaging solution with reduced sensor rigidity requirements compared to conventional imaging solutions. In this invention, the sensor array need not be rigid.

It is an object of this invention to provide an imaging solution for use with a broad set of applications. Applications for this invention include, but are not limited to applications such as biometrics, three-dimensional iris scanning, object recognition, long-range dimensional metrology, remote inspection, and 3D microscopy.

BRIEF DESCRIPTION OF THE SEVERAL VIEWS OF THE DRAWING

FIG. 4a shows one embodiment of constructing a virtual reference point with a transparent curved surface;

FIG. 4b represents the autocorrelation produced with a virtual reference point;

DETAILED DESCRIPTION OF THE INVENTION

Figure 1A:
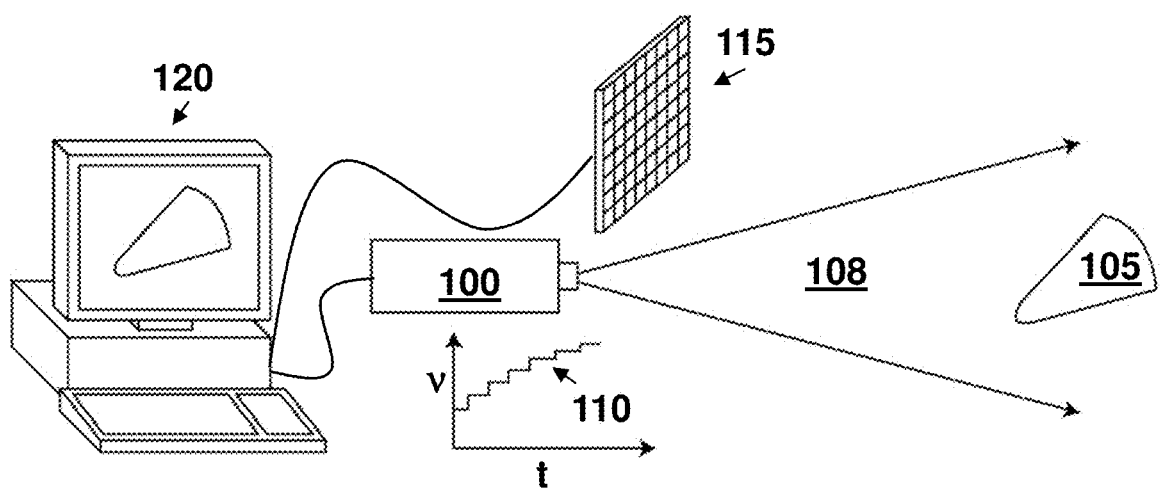
FIG. 1a shows a schematic diagram of one embodiment of a system for imaging of objects according to the present invention.

Described are a wide array of systems and methods for remote sensing of objects. However, it will be appreciated that the inventive concepts disclosed herein are not limited to the specific embodiments disclosed. For example, the general techniques disclosed herein may be usefully employed in any environment where precise, three-dimensional data might be usefully captured and processed, including ophthalmology, material inspection, manufacturing, flight systems, surveillance, and remote sensing. In addition, while numerous variations and implementations of remote sensing are described, it will be appreciated that other combinations of the specific illuminating, sensing, processing, and reconstruction techniques described herein may be used, and that such variations are intended to fall within the scope of this disclosure.

Terms and Definitions

To provide greater clarity and ease of comprehension, as well as to avoid ambiguities in wording and confusion of nomenclature, the following titles, terms and definitions are provided in addition to the terms as commonly used in the art.

Surface Scattering Function: A mathematical representation of an object based on the reflection of radiation off the surface of the object. A sufficient mathematical model for the purposes of this application is to describe the surface of a three-dimensional shape by a complex surface scattering function $g(x, y, z)$. The support of the function, meaning the positions in space where the function is non-zero, represents surface locations. The magnitude and phase of the function at these locations represent, respectively, the scattering strength and the phase change imparted on the reflected wave. Shadowing from the object is normally taken into account so that the function is zero-valued for surfaces that are not illuminated. The magnitude of the surface scattering function may also be adjusted to account for a non-uniform illumination beam.

Speckle Pattern and Speckle Pattern Intensity: Reflected radiation from objects with rough surfaces produces a speckle pattern whose intensity pattern varies spatially due to interference between different contributions to the optical field at a given observation point. The speckle pattern also varies with frequency ν or wavelength λ of the illuminating laser. Thus, the intensity at an observation point can be represented by the function $I(x, y, z; v)$. A speckle pattern is typically, but not necessarily, measured on a nominally flat surface in space. If there is no relative motion or atmospheric turbulence, then the speckle intensity is constant in time.

Data Cube: The speckle pattern intensity sampled at positions in space at different values of laser frequency forms a data cube. Typically, and in this description, a data cube refers to the speckle pattern intensity measured on a detector array at discrete values of laser frequency. A data cube need not have the same number of elements in each of the three dimensions. The term data cube may refer to a set of speckle pattern intensity data that is remapped onto a three-dimensional array in order to more uniformly sample Fourier space on a regular grid (see "Applications of Tunable Lasers to Laser Radar and 3D Imaging," L. G. Shirley and G. R. Hallerman, MIT Lincoln Laboratory Technical Report 1025, 26 Feb. 1996, for a discussion of sampling Fourier space).

Autocorrelation: The autocorrelation $P(x, y, z)$ of the complex three-dimensional function $g(x, y, z)$ is defined mathematically as:

$$P(x, y, z) = \int_{-\infty}^{\infty} \int_{-\infty}^{\infty} \int_{-\infty}^{\infty} g^*(x', y', z')g(x+x', y+y', z+z') dx' dy' dz'.$$

This mathematical definition describes the autocorrelation of a function as being the sum of a series of copies of the function with each point in the function being placed sequentially at the origin of the autocorrelation coordinate system and weighting the copies by the complex conjugate of the value of the function at the point that is placed at the origin. It is known that within certain approximations, the three-dimensional Fourier transform of a data cube provides an estimate of the autocorrelation P(x, y, z) of the surface scattering function representing the three-dimensional shape of the target. In general, the autocorrelation function is complex valued. Here, we are mainly interested in the support (meaning positions where the function is non-zero) and the magnitude of the autocorrelation function at these support points. Therefore, we use the term autocorrelation function to denote the magnitude of P(x, y, z). The term autocorrelation also includes averaging the autocorrelation, meaning the average of a quantity related to the magnitude of P(x, y, z), for a set of data cubes from different realizations of the speckle pattern intensity. The realizations may be obtained, for example, from slightly different viewing geometries, often produced by a small relative rotation of the object, or by sampling Fourier space at different beginning wavelengths. For example, a large data cube may be divided into two or more smaller data cubes for the purpose of averaging. Two examples of averaging are taking the average of the magnitude and the root-sum-square average of the magnitude of P(x, y, z). Given a particular copy of the surface scattering function, points on the support of the autocorrelation can be divided into two groups: autocorrelation points that lie on the copy, and autocorrelation points that do not lie on the copy. The support of the autocorrelation contains the complete copy.

Copy and Inverted Copy: A copy is a translated version of the function g such that a support point of g lies on the origin. In this description, a copy also refers to the point-by-point magnitude of the translated copy. If we think of the surface scattering function as comprising a set of N discrete scattering points denoted by amplitudes $g_1, g_2, \ldots g_N$ occurring at the positions $(x_1, y_1, z_1), (x_2, y_2, z_2), \ldots (x_N, y_N, z_N)$, then we can write $$P(x, y, z) = \sum_{n=1}^{N} g_n^* g(x + x_n, y + y_n, z + z_n),$$

which can be interpreted as N shifted copies of the scattering function g. The nth copy is obtained by shifting the scattering function such that point n lies at the origin. The copy is weighted by the complex conjugate $g^*_n$ of the amplitude of the point that is set at the origin. (In practice, it is sufficient to represent a continuous surface as a set of discrete points since all three-dimensional images have practical resolution limits.) Alternatively, P(x, y, z) may be written as $$P(x, y, z) = \sum_{n=1}^{N} g_n g^*(-x + x_n, -y + y_n, -z + z_n),$$

which can be interpreted as N inverted and complex conjugated copies of the scattering function, where inverted refers to flipping the sign of the function in all three dimensions. Thus, we can think of P(x, y, z) as being comprised of multiple shifted copies or of multiple shifted inverted complex conjugated copies of the scattering function. The different embodiments of the invention relate to forming a three-dimensional image by extracting a copy or an inverted copy of the scattering function from the autocorrelation function. Since the phase of the scattering function g is relatively unimportant in representing a three-dimensional image, we use the term copy to refer to an estimate of the support and magnitude of g. The primary objective of three-dimensional imaging is to determine the location of the surface or the support of g. A secondary objective is to estimate the magnitude of the scattering function on the surface. We will not distinguish between copy and inverted copy unless it is necessary to do so. We will typically consider the reconstruction of either the copy or the inverted copy to be a solution since one can be obtained from the other.

Interference Events: Light scattered from two points on the surface of the object interferes to produce a corresponding contribution at two points in the autocorrelation. If a vector is formed whose end points are the two scattering points, then the position of one of the corresponding points in the autocorrelation is determined by placing one end of the vector on the origin of the autocorrelation. The second point in the autocorrelation, which is symmetric about the origin, is determined by placing the other end of the vector at the origin. The term interference event refers to the interference of two points on the object producing a given point in the autocorrelation function. If a given point in the autocorrelation is produced by only one pair of points on the object, then it is termed a single interference event. If a point in the autocorrelation function is produced by multiple interference events, then these individual contributions interfere producing a point on the autocorrelation function whose magnitude depends on the relative phases and strengths of the individual contributions. Thus, different speckle realizations may produce widely varying magnitudes at points where multiple interference events occur. Some of these points may have very low values, or dropouts, that are masked by noise. Averaging the autocorrelation as described above tends to fill in these dropouts. One can locate points in the autocorrelation function arising from single interference events or a low number of interference events by calculating the variation of the estimates used to form the averaged autocorrelation function. Points arising from single interference events tend to have lower variance. Points near the origin of the autocorrelation tend to be produced from many interference events.

Brightness: The magnitude of a point in the autocorrelation relative to other points in the autocorrelation. It also refers to the relative magnitude of autocorrelation points resulting after one or more shift-and-compare operations.

Bright Copies: Copies that are produced in the autocorrelation by placing bright points in the surface scattering function at the origin. Bright points in the autocorrelation that are not too close to the origin tend to be produced by interference events involving bright points on the surface scattering function.

Projected Reference Point: A spot of focused coherent radiation that is projected onto the surface of the object in addition to a wider-area illumination beam, the illumination beam being created by a source of coherent radiation. The projected reference point may be an illumination spot of reduced size on an object relative to an illumination beam, or illumination spot on said object. The projected reference point influences the speckle pattern intensity in a manner that carries useful information. The spot can be formed by a means of controlling the illumination beam to produce a separate, optical beam that arrives at the surface of the object at a delayed or earlier time than the wider-area illumination beam. The means of controlling the illumination beam can include a lens to move and focus the beam and the means of controlling can also include a means for optically splitting a single source of radiation creating two beams and delaying one beam's illumination of the object relative to the other beam. The position of the projected reference point on the object can also be varied by moving the source of radiation relative to a focusing element. For example, if the source of radiation is the tip of a fiber, one means for moving the projected reference point on the surface of the object is to move the tip of the fiber sideways with a piezoelectric positioner. The projected reference point produces a copy in the autocorrelation that is separated from the central area of the autocorrelation. If the time delay between the illumination beam and the beam forming the projected reference spot is greater than twice the corresponding range extent of the illuminated region of the object, then the copy produced by the projected reference point will be completely separated from and distinct from the central region of the autocorrelation.

Curved Surface Creating a Reference Point: A surface that reflects a portion of an illumination beam while allowing most of the illumination to strike the object, the illumination beam being created by a source of coherent radiation. The curved surface produces a virtual reference point that is offset from the object in range and that influences the speckle pattern intensity in a manner that carries useful information. Provided that the curved surface is sufficiently far away from the object, the virtual reference point forms a distinct copy in the autocorrelation that is separated from the central region of the autocorrelation.

Regional Image Selection Technique: The process of forming a three-dimensional image of an object without performing a reconstruction by selecting a region in the autocorrelation function that contains a copy that is separated and distinct from the central region of the autocorrelation. The copy is typically formed by a real or virtual reference point that is offset in range. The copy is offset from the central region of the autocorrelation and can be selected by cropping the autocorrelation to include only the copy.

Change Detection: The process of comparing autocorrelations of two similar objects or of a single object at different times and observing differences in the autocorrelations. These differences in the autocorrelation are related to changes in the object or variations between objects.

Rotate and Compare: The process of obtaining autocorrelations of an object at slightly different angles and rotating one autocorrelation with respect to the other by the angle between the two measurements such that the two autocorrelations overlap. The two autocorrelations are then compared point by point. Regions that are supported in one autocorrelation and not the other are related to points that have become shadowed or have become visible due to the relative rotation of the object between measurements. Varied support regions may also be due to specular returns that are present for only one of the measurements. For example, if a bright point or specular reflection occurs in one measurement and not the other, then the difference between these two measurements will provide an estimate of a copy.

Physical Feature of an Object: A structure in similar objects that varies between these objects and produces differences in the autocorrelation that can be measured without performing a reconstruction. Identification, recognition, or classification of these objects can be performed based on comparing the differences in the autocorrelation arising from differences in the features occurring between objects. Physical features can be localized or distributed over the surface. A localized feature of an object is termed a partial representation of the object. It can be determined that a given localized feature is not contained in the object if the autocorrelation does not contain all of the support points of the autocorrelation of the feature taken by itself. Rotating and comparing may be required to align the coordinate systems.

Time Gating: The process of gating a receiver or sensor in conjunction with a pulsed laser train in a manner that blocks out backscattered radiation in range intervals not associated with a region of interest. For example, background radiation that overfills an object and strikes a background surface occurring at a greater range may be removed by time gating. In addition, certain range slices of the object may be isolated by time gating. Isolating range slices of a controlled width often produces regions of interest on the object with spatial holes because corresponding regions of the surface fall outside of the range slice. Surfaces with holes produce more sparsely populated autocorrelations that simplify the process of reconstructing a copy from the autocorrelation. Individual range slices can be reconstructed separately and then combined together to form an image with high range resolution.

Shift-and-Compare: The process of selecting a support point of the autocorrelation, shifting the origin of the autocorrelation to this point and doing a point-by-point comparison between the shifted and the original autocorrelations. It can be proven that the overlap of the support of the shifted and original autocorrelation function contains at least one intact copy and one intact inverted copy. The term shift-and-compare also refers to the process of comparing the shifted autocorrelation with the result of a previous shift-and-compare operation. It also refers to a series of shift-and-compare operations whether performed one at a time sequentially or in parallel. The comparison operation may comprise decision rules for determining when to discard points and how to adjust the brightness of a partial reconstruction. If a shift lies on a copy, then a shift-and-min operation tends to eliminate points not lying on the copy while preserving points that do lie on the copy. A shift-and-min operation tends to refine a partial reconstruction if the shift is a good shift.

Partial Reconstruction: A resulting set of autocorrelation points that have survived all prior shift-and-compare operations. The objective of a set of shift-and-compare operations is to form a partial reconstruction that approximates a copy and can be used as a representation of the object.

Shift: The term shift used as a noun refers to the point on the support of the autocorrelation to which the origin is translated, or offset, before comparing in a shift-and-compare operation.

Shift: The term shift, when used as a verb, refers to the offsetting of a point relative to another point. In this description, shift is commonly used to define the action of offsetting the origin of an autocorrelation to another autocorrelation point.

Initial Shift: The first shift used in a sequence of shift-and-compare operations.

Shift Candidates: Autocorrelation points on the support of the autocorrelation that are being considered for future shifts. Shift candidates must have survived all previous shift-and-compare operations and therefore are taken from the list of points in the partial reconstruction. The crux of forming a partial reconstruction that approximates a copy is to select shift candidates to be used as shifts that lie on the copy being reconstructed. In the noiseless case, it can be shown that all points on the copy survive shifts selected from the copy being reconstructed. Thus, as additional shifts cause autocorrelation points not on the copy to be discarded or eliminated, the partial reconstruction tends to approach a copy.

Good Shift Candidate: A point from a list of shift candidates that lies on the copy being reconstructed, also referred to as a good shift.

Intersect Operation: The operation of taking the intersection or the logical "and" of the set of shifted autocorrelation points and the partial reconstruction (or the autocorrelation for a first shift) that overlap during a shift-and-compare operation. This operation is especially amenable to rapid processing using single bit representations of the autocorrelation, where brightness values above and below a threshold are set to 1 and 0, respectively.

Minimum Operation: The operation of taking the minimum of the set of autocorrelation points that overlap during a shift-and-compare operation.

Brightness-Ranking Operation: The operation of ranking, by brightness, the autocorrelation points that overlap during a set of shift-and-compare operations. The decision to discard or eliminate an autocorrelation point can be delayed in order to mitigate noise. For example, a point might be discarded after a given number of shift-and-compare operations has occurred and a certain percentile of the ranking has fallen below a threshold value.

Shift-and-Intersect: A shift-and-compare operation where the comparison is an intersect operation. By intersect operation is meant the conventional mathematical intersection of two sets. A shift-and-intersect operation is useful for rapidly exploring choices of shifts and for finding initial shift candidates with few survivors.

Shift-and-Min: A shift-and-compare operation where the comparison is a minimum operation. By minimum operation is meant the conventional mathematical minimum of a set of numbers corresponding to brightness. This operation tends to form a brightness distribution that correlates with the magnitude of the surface scattering function. The process cannot be continued indefinitely, however, because as dimmer points on the copy are used as shifts, the brightness of the partial reconstruction decreases and "melts" into the noise floor. Therefore, the shift-and-min operation is typically applied to brighter shifts.

Shift-and-Rank: A shift-and-compare operation where the comparison is a brightness-ranking operation. A brightness ranking consists of sorting points according to brightness. This operation also tends to form a brightness distribution that correlates with the magnitude of the surface scattering function but is more forgiving of noise.

Survivors: Autocorrelation points that are not eliminated by a shift-and-compare operation or a set of shift-and-compare operations.

Breaking Symmetry: Choosing a good shift candidate that lies on either the copy or inverted copy but not both and then running that shift to eliminate points on the copy not being selected. Since the initial shift produces both a copy and in inverted copy, a decision needs to be made about which one to reconstruct. The copy and inverted copy are point symmetric to within an offset so that the copy can be calculated from the inverted copy and vice versa. Thus, it is not important in the reconstruction process whether the copy or inverted copy is reconstructed.

Column: The z dimension in the autocorrelation or a partial reconstruction corresponding to range, where the range direction corresponds to the direction between the receiver, or sensor, and the object. The term column also refers to a column in a data cube, with the position in the column corresponding to wavelength or frequency.

Preferred Shift Candidates: Shift candidates that are selected according to rules and that are likely to be effective at removing points in the partial reconstruction that do not lie on the copy being reconstructed when performing a shift-and-compare operation. For example, the initial shift may be selected from a list of preferred shift candidates obtained from the entire autocorrelation, and the list of preferred shift candidates for subsequent shift-and-compare operations may be selected from the intersection of the partial reconstruction and the original list of preferred shifts. Additionally, new preferred shift candidates not in the above list may be determined at any step of the process. Following are some illustrative examples of rules or procedures for generating lists of preferred shift candidates.

Locating Local Peaks: Locating autocorrelation points in the autocorrelation or the partial reconstruction that are brighter than all nearest-neighbors.

Locating Separated Peaks: Locating autocorrelation points with peaks in the autocorrelation or the partial reconstruction that are greater than all neighbors within a given radius or that are greater than any local peaks within a given radius.

Locating Perimeter Points: Locating autocorrelation points on or near the perimeter of the support of the autocorrelation whose brightness is above a threshold.

Locating Extreme Perimeter Points: Locating perimeter points that are further away from the origin than neighboring perimeter points or that have larger $|x|$, or $|y|$, or $|z|$ values than neighboring perimeter points.

Locating Potent Points: Locating autocorrelation points that when used as an initial shift produce a relatively small number of survivors.

Locating Spreading Points: Locating autocorrelation points that when used as an initial shift produce a large separation between the copy and inverted copy.

Locating Low Interference Points: Locating autocorrelation points in the autocorrelation that arise from a single interference event or a low number of interference events.

Opacity Constraint: A mathematical representation of the reflective properties of a surface where the scattering function is a single-valued function of x and y. An object with an opacity constraint is one whose surface scattering function is a single-valued function of x and y. If the sampling resolution in x and y is sufficiently fine compared to the sampling resolution in z (or alternatively the surface slope is not too large) then each x-y cell in the measurement will have contributions from only one range cell. In this case the, the support of the autocorrelation along the z-axis is limited to the origin. Using this fact, one can determine from inspection of the autocorrelation whether the opacity constraint is realized. If it is, then it can be used to help determine good shifts. For example, if there is only one support point in a column of a partial reconstruction and it is known that the partial reconstruction should have a surface at that location, then the support point must be a good shift.

Geometrical Assumptions: Assumptions about the shape of the object that can be helpful in the selection of good shifts. For example, if the object is composed of geometrical elements, including, for example, planes, cylinders, cones, and spheres, then once these surface elements begin to appear in the partial reconstruction, new shift candidates can be generated by continuing these shapes by interpolation or extrapolation and finding points on the partial reconstruction that lie on or near these surfaces. Furthermore, if a CAD model (or any mathematical model) of the object or features on the object exists, then new shift candidates can be generated once features in the CAD model begin to appear. Additionally, a previous measurement of the object can be used as a mathematical model upon which to select new shift candidates based on finding points in the partial reconstruction that match the model.

Cluster of Shift Candidates: A set of shift candidates known to contain at least one good shift.

Vector Matching: A method for selecting a cluster of shift candidates. The method consists of selecting a vector formed by the origin and a support point of the autocorrelation and tagging those points in the partial reconstruction where the vector endpoints fit into the support points of the partial reconstruction. One method for obtaining and tagging these fit points is to sequentially place one end of the vector on each support point of the partial reconstruction. If the other end of the vector aligns with a support point of the partial reconstruction then both points in the partial reconstruction are tagged. Typically the support point is chosen to be a perimeter point or an extreme perimeter point in order to produce a vector that fits into a minimum number of locations in the partial reconstruction. Since the support point in the autocorrelation from which the vector is formed arises from an interference event, the vector must fit into the partial reconstruction in at least one place, and at least one of these fits must lie on the copy. Therefore, it is guaranteed that the process produces a cluster of shift candidates.

Union Operation: The operation of taking the point-by-point union or logical "and" of a set of shift-and-compare operations. It is applied to a cluster of shifts to ensure that the no good points are eliminated. A point must be eliminated by all the shift-and-compare operations in order to be eliminated from the partial reconstruction. This operation is especially amenable to rapid processing using single bit representations of the autocorrelation, where brightness values above and below a threshold are set to 1 and 0, respectively.

Maximum Operation: The operation of taking the point-by-point maximum of a set of shift-and-compare operations. It is applied to a cluster of shifts to ensure that the no good points are eliminated. A point must be eliminated by all the shift-and-compare operations in order to be eliminated from partial reconstruction.

Start: A set of good shifts lying on a copy. Typically, the start consists of a small number of shifts. If it is not clear how to proceed or the start lies on a copy that is not a bright copy, then it may be advantageous to stop the process and save the start for later use. Individual starts may be combined and starts, or combined starts, may be translated to bright copies to mitigate noise.

Self-consistent points: A set of autocorrelation points that collectively survive a set of shift-and-compare operations when all points are used as shifts. Although self consistency does not guarantee that all points lie on the same copy, a large set of self-consistent points is likely to lie predominantly on the same copy.

Consistency Matrix: A matrix indicating the self-consistency of all possible combinations of point pairs in a list of shift candidates. The matrix may be formed by assigning an index number to each point in the list and using these indices as row and column headings of a two-dimensional array. If a point pair is self-consistent, then the corresponding element of the array is set to 1 or True. If the point pair is not self-consistent, then the corresponding element of the array is set to 0 or False. The rows or columns of the array can be generated efficiently by doing a shift-and-intersect operation for the corresponding shift and seeing which of the points on the list survive.

Matrix Reordering: The process of changing the order of the elements making up the row and column headings of a consistency matrix so as to create a large block of self-consistent points.

Error Testing: The process of testing whether the partial reconstruction is mathematically consistent with the autocorrelation. In some cases it may be necessary to choose shifts that are not guaranteed to be good shifts. In this case, it may be necessary to perform a test to try to determine if one or more bad shifts have been used. Then the process can be stopped and picked up before the error occurred so that a new path for choosing shifts can be explored. Error testing can take many forms. One method is to test whether the support of the autocorrelation of the set of shift points produces points that are not in the autocorrelation. Another method is to calculate the autocorrelation of the partial reconstruction to see if all points in the measured autocorrelation are spanned by this new autocorrelation. This approach becomes more effective later in the process after the number of points in partial reconstruction has been reduced. Yet another approach is to test whether the extent of the partial reconstruction along each of the three axes is sufficiently large to span the width of the autocorrelation in the same direction.

Cross Matching: The process of comparing two or more starts and calculating an offset between them that puts the shifts corresponding to these starts on the same copy, thus combining two or more starts into a single larger start. The entire start can now be run as shifts in a shift-and-compare operation, producing a partial reconstruction having fewer extra points.

Translating Starts to a Bright Copy: The process of translating a start or a combined start so that it lies on a bright copy, which may be, ideally, the brightest copy.

Range Filtering: The process of eliminating extra points along a column in a partial reconstruction after the final shift-and-compare operation has been performed. If the brightest copy is being reconstructed, then it is likely that the brightest residual point in the column occurs at the correct z value in the column for the copy being reconstructed.

Processor: A processor, as used in this description is defined as hardware, software, or any combination of these suitable for processing the three-dimensional imaging and reconstruction means and methods described herein. This includes realizations in one or more microprocessors, microcontrollers, embedded microcontrollers, programmable digital signal processors or other programmable device, along with internal and/or external memory. This may also, or instead, include one or more application specific integrated circuits, programmable gate arrays, programmable array logic components, or any other device or devices that may be configured to process electronic signals. It will further be appreciated that a realization may include computer executable code that may be stored, compiled or interpreted to run on one of the above devices, as well as heterogeneous combinations of processors, processor architectures, or combinations of different hardware and software. At the same time, processing may be distributed across devices such as a radiation source, a sensor and/or computer in a number of ways or all of the functionality may be integrated into a dedicated, standalone image capture device. All such permutations and combinations are intended to fall within the scope of the present disclosure.

DESCRIPTION

Figure 1B:
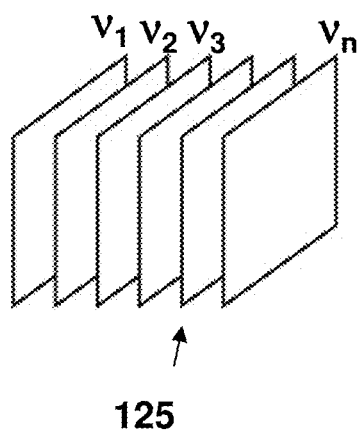
FIG. 1b shows one embodiment of a graphic representation of collected data which includes a series of two-dimensional arrays with each representing observed intensity values at a particular wavelength.

In reference to FIG. 1a, one embodiment of the invention includes a tunable laser 100 illuminating object 105, whose three-dimensional shape is being measured, with a laser beam 108. Laser beam 108 may overfill object 105 or may spot illuminate a region of interest on object 105. Laser frequency 110 of laser beam 108 varies in time so as to produce a spatially varying speckle pattern intensity on a detector array 115. Processor 120 receives speckle pattern intensity measurements from detector 115 and processes this information from detector array 115 to produce a digital representation of the three-dimensional image of object 105. In reference to FIG. 1b, intensity measurements from detector array 115 are converted into a data cube 125 of intensity values at a discrete set of laser frequencies. The three dimensional Fourier transform of data cube 125 is calculated by processor 120 and produces an estimate of the autocorrelation of the surface scattering function representing the three-dimensional shape and scattering properties of object 105. In one embodiment, laser 100 is a CW laser and frequency 105 is stepped approximately linearly in time. In another embodiment, laser 100 is a CW laser and frequency 110 is scanned approximately linear in time. In yet another embodiment, laser 100 is a pulsed laser and frequency 110 steps approximately linearly between pulses or sets of pulses. In a further embodiment, laser 100 is pulsed and detector array 115 is time gated. Time gating allows light in range intervals not associated with a region of interest to be blocked, thus minimizing clutter or selecting particular range slices of the target. In yet another embodiment, multiple laser frequencies are emitted simultaneously and detector 115 contains wavelength selective elements to cause different detector elements in detector array 115 to be sensitive to different laser frequencies. In one embodiment, tunable laser 100 is an external cavity diode laser, in another embodiment laser 100 is a frequency modulated laser. In yet another embodiment, laser 100 comprises a set of lasers operating at a set of discrete wavelengths.

Although the source of coherent radiation in one embodiment comprises laser radiation creating laser beams, it is understood that the invention is capable of utilizing other coherent radiation sources such as, but not limited to all forms of electromagnetic radiation, ultrasonic radiation, and acoustic waves.

Figure 1C:
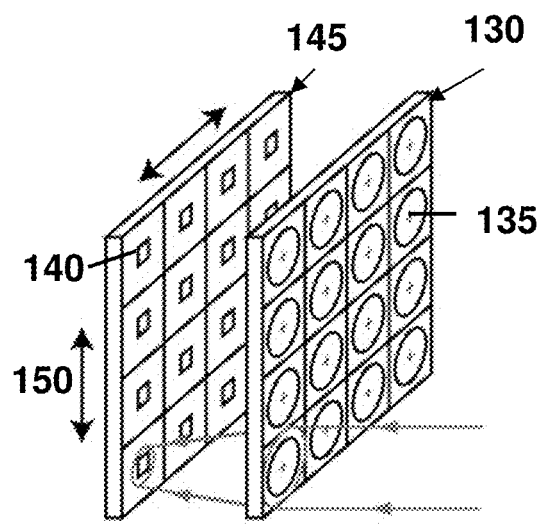
FIG. 1c shows a representation of one embodiment of a sensor used to collect speckle patterns and intensity values.

In reference to FIG. 1c, in one embodiment, detector array 115 comprises a front structure 130 that contains an array of lenses 135. Lenses 135 may be ordinary lenses, or in order to reduce weight, size, and cost may be flat-panel lenses including, for example diffractive lenses, holographic lenses, or Fresnel lenses. Lenses 135 condense the speckle pattern intensity at the various regions of front structure 130 to fill detector arrays 140 which are distributed in a matching array on back structure 145. Front structure 130 and matching back structure 145 need not be square and need not comprise rectangular arrays of lenses 135 and detector arrays 140. In one embodiment, front structure 130 comprises only one lens 135 and back structure 145 comprises only one detector array 140. Condensing of the speckle pattern may be achieved, for example, by using a separation between front structure 130 and back structure 145 such that the light entering lens 135 does not come to a focus on but fills detector 140. The advantage of using an array of detectors 140 is that the speckle pattern intensity distributed over the large of front structure 130 can be mapped onto a number of small and efficient detector arrays 140 with many detector elements. Lenses 135 or detector arrays 140 may include wavelength selective filters or coatings that block light with wavelengths that lie outside of the tuning range of the laser, thus reducing background noise due to ambient light. Back structure 145 may translate laterally 150 relative to front structure 130 to effectively steer the receiver array and achieve fine pointing control without rotating the entire structure.

Although embodiments of the system herein describe detectors 140 as being optical devices, detectors 140 may be any individual, array or any combination of detectors, sensors or other devices capable of detecting radiation at the operational wavelength of radiation source 100. In one embodiment, detectors 140 are CCD arrays, in another embodiment, detectors 140 are CMOS arrays, in yet another embodiment, detectors 140 are electron-multiplied CCD arrays. In one embodiment, detector arrays 140 comprise Geiger-mode avalanche photodiode arrays.

In one embodiment, laser 100 rapidly emits a plurality of wavelengths. Rapid emission of a plurality of wavelengths may be necessary in cases where there is a relative rotation between laser beam 108 and object 105 during laser frequency scan 110 or where atmospheric turbulence causes the speckle pattern to fluctuate on the time scale of frequency scan 110.

Figure 2:
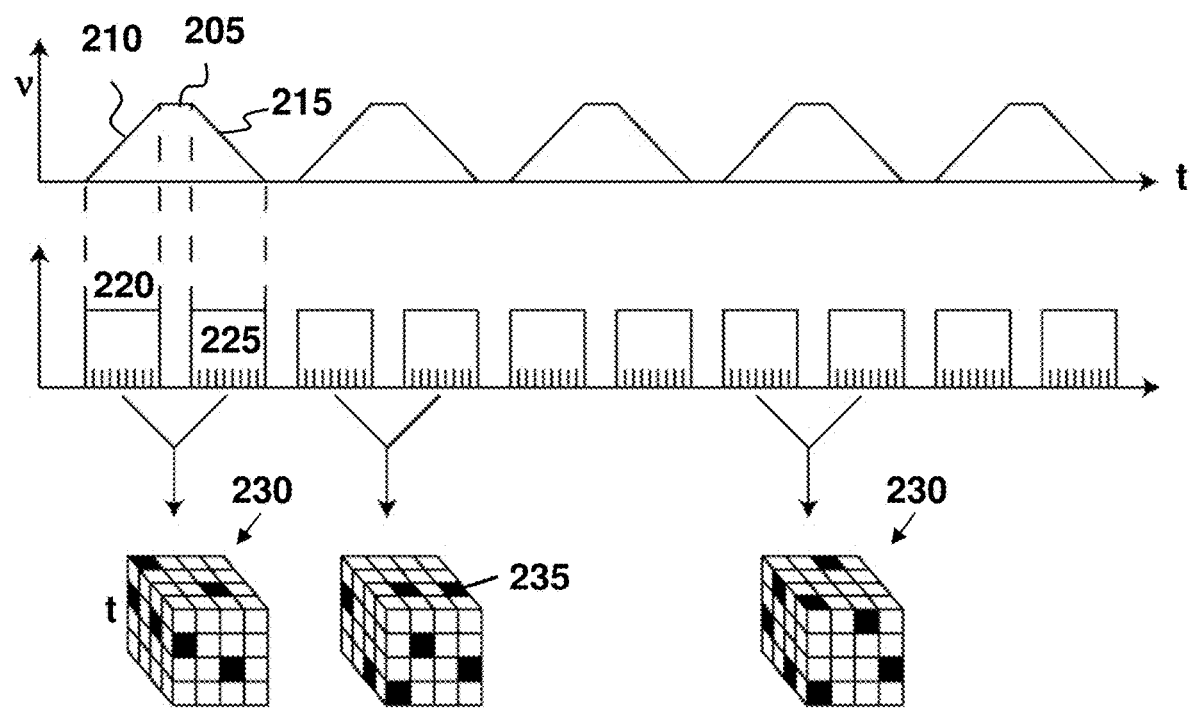
FIG. 2 shows a graphical representation of one embodiment of a radiation source rapidly emitting a plurality of wavelengths, the source of radiation being synchronized with a receiver creating data representing speckle patterns and intensity values.

FIG. 2 illustrates one embodiment of a system and method for use in speckle imaging that can provide the type of data to be used in this invention. This embodiment of the invention employs a frequency scan 110 that is a repetitive rapidly changing waveform 205. Rapid repetition of the waveform allows for autocorrelations to be produced from single waveform elements consisting of up-chirps 210 and down-chirps 215 or from combinations of small sets of these waveform elements in time frames that are less than the speckle coherence time produced by relative target rotations or atmospheric turbulence. These autocorrelations can be averaged to build up the signal-to-noise ratio of the resulting averaged autocorrelation. Waveform elements 210 and 215 may exist in any combination and waveform 205 may be comprised entirely of up-chirps 210 or down-chirps 215. In one embodiment, waveforms 205 change frequency approximately linearly in time. In another embodiment, waveforms 205 are stepped in frequency. In yet another embodiment, laser 100 is pulsed and waveforms 205 vary with approximately linear frequency steps between pulses or sets of pulses.

In one embodiment, detector arrays 140 are avalanche photodiode arrays that count photons. In another embodiment detector arrays 140 are avalanche photodiode arrays with timing circuits that mark the time of arrival of the first photon. Avalanche photodiode arrays allow for very sensitive detection at single-photon levels. In one embodiment, the time of arrival of the first photon in a given pixel of the detector array during the time period 220 where the detector is armed and counting is correlated with the frequency or wavelength of that photon by noting in which time bin 225 the photon arrived at that pixel. Thus wavelength information can be obtained from timing without requiring that a frame of speckle data be read out for each laser wavelength. This embodiment allows for very rapid acquisition of data cubes 230 at very low photon counts. Each column in data cube 230 corresponds to a pixel in detector array 140. The blackened voxels 235 in data cube 230 represent the pixels and timing bins where a photo-electron is detected. The size of data cube 230 can be extended laterally by combining data cubes 230 corresponding to the different detector arrays 140. In some types of avalanche photodiode arrays, individual pixels that have produced a photo-electron can be rearmed during time period 220 so that photons at multiple wavelengths can be detected at a single pixel during time period 220. In another type of avalanche photodiode array, a pixel that has detected a photo-electron is dead until the entire array is reset at the next cycle corresponding to a new time period 220. In this case, only one photo-electron can be detected per column of the data cube and the probability of detection decreases towards the right end of time period 220 because of this so-called saturation effect. In one embodiment, the saturation effect is mitigated by combining the counts from both an up-chirp 210 and a down-chirp 215 so that the probability of detection for the combination 205 is more evenly distributed over different laser frequencies making up waveform 205. In another embodiment, there are extra pixels in detector array 140 so that an individual speckle is over sampled. Thus, the resulting macro-pixel that is formed by combining results for a given range bin in a block of pixels can have more than one count. In one embodiment a data cube is generated from multiple timing cycles. The number of time periods 220 that can be combined into a single data cube is determined from the timescale of the speckle fluctuations due to influences such as relative target rotation and turbulence.

A three-dimensional Fourier transform of each data cube 230 is generated by a processor in order to produce an estimate of the autocorrelation for averaging. Methods of generating Fourier transforms are well known in the art and all are contemplated for use in this invention. In one embodiment, averaging is achieved by calculating the root-mean-square average of the magnitudes of the individual Fourier transforms of data cubes 230. In another embodiment, the average of the magnitudes of the Fourier transforms are calculated. In one embodiment, the Fourier transforms are calculated via the Fast Fourier Transform (FFT) algorithm. In another embodiment the Fourier transforms are calculated via a Discrete Fourier Transform (DFT), which may be more efficient when the total number of photo-electron counts in a data cube is small.

In one embodiment of the invention, motion of the speckle pattern intensity arising from relative rotation of object 105 with respect to laser beam 108 is compensated for by remapping the speckle pattern intensity within a data cube to account for motion of the speckle pattern intensity during a frequency scan 110. This mapping may occur between elements of the composite data cube arising from individual detector arrays 140. The primary effect of relative rotation is to shift the speckle pattern intensity across detector 115. Remapping of the speckle pattern intensity reduces the requirements on the speed of laser frequency scan 110 and allows more time periods 220 to be combined coherently to produce data cubes 230.

In another embodiment of the invention, motion of the speckle pattern arising from relative rotation of object 105 with respect to laser bean 108 is used to synthesize a larger effective aperture. Thus, the lateral resolution of the three-dimensional image can be extended beyond the size limitations of detector array 115.

In another embodiment, the speckle pattern intensity is remapped when forming a data cube to more linearly sample Fourier space. For example, speckle size is proportional to the laser wavelength and rescaling the speckle size so that it remains constant during a scan improves the lateral resolution of the three-dimensional image.

FIGS. 3a, 3b, 4a and 4b illustrate embodiments of the systems and methods that provide for projected and virtual reference points that can be used by a regional image selection technique to construct a representation of an object.

Figure 3A:
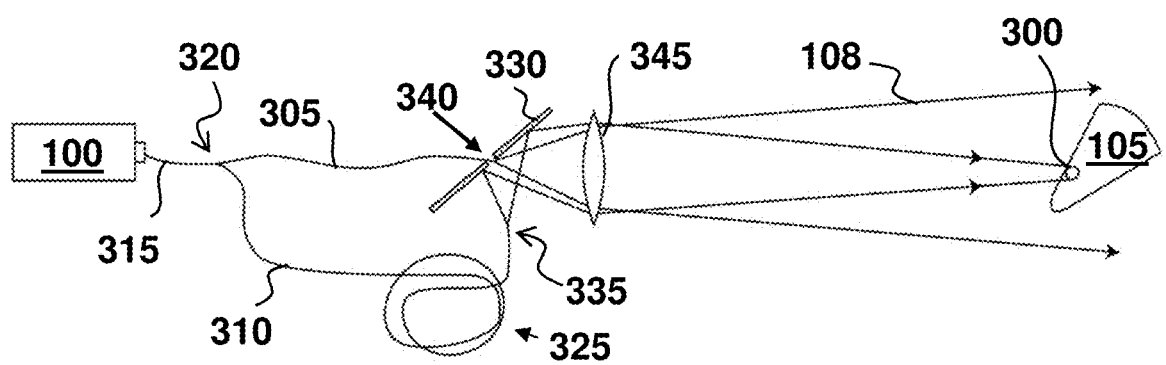
FIG. 3a shows a schematic diagram of one embodiment of a radiation source projecting a reference spot.

Referring to FIG. 3a, in one embodiment of the invention, projected reference point 300 is projected onto the surface of object 105 in addition to laser illumination from laser beam 108. Projected reference point 300 is formed by optically splitting light from laser 100 into path 305 and path 310, delaying one path with respect to the other by causing it to follow a longer path, and focusing one path to produce projected reference point 300. In one embodiment spitting is accomplished by coupling laser 100 into fiber 315 and using fiber splitter 320 to produce paths 305 and 310. The delay 325 is produced by using different lengths of fiber before recombining the beams. In one embodiment the beams are recombined by reflecting the light from path 325 off of pin-hole mirror 330 and directing light from path 305 through the hole in pin-hole mirror 330. Fiber ends 335 and 340 are positioned such that light from both paths passes through lens 340 and one path produces projected reference spot 300 while the other path produces illuminating laser beam 108. In another embodiment, paths 305 and 310 do not overlap at the transmitter. Fiber ends 335 and 340 are offset laterally with each beam passing through its own lens such as to produce projected reference spot 300 and illumination beam 108. In one embodiment lens 345 is replaced with a curved mirror. Likewise, in the embodiment using two different lenses, one or both of these lenses may be replaced with a curved mirror. This embodiment shows an example of sources of the coherent radiation outputting the wavelengths being fiber ends 335 and 340 each outputting the wavelengths.

Due to the optical path delay associated with projected reference point 300, the light backscattered from the region of object 105 illuminated by projected reference point 300 arrives as if this light came from a surface patch that is offset in range. The introduction of projected reference point 300 influences the speckle pattern intensity in a manner that carries useful information about object 105. In reference to FIG. 3b, if the delay between paths 305 and 310 is sufficiently large, then copy 350 and inverted copy 355 produced by scattering points associated with projected reference point 300 will be offset from and will not overlap with the central autocorrelation 360 that would be formed by object 105 without projected reference point 300. Thus projected reference point 300 produces a copy and inverted copy that appear automatically in the autocorrelation and can be extracted from the autocorrelation by a regional image selection technique.

Because projected reference point 300 has a finite size and may illuminate numerous scattering cells on the surface of object 105, the three-dimensional image formed by the projected reference point will contain closely spaced copies, thus causing a blur and decreasing the lateral resolution of the image. In one embodiment of the invention, the image quality is improved by moving fiber end 335 sideways in such a way as to move the projected reference point to different regions of the surface of object 105. By doing so, favorable positions of the projected reference point may be determined where the spot falls on a region of the surface producing a glint or a specular reflection. In one embodiment, fiber motion is produced with a piezoelectric actuator. Since the backscattered light from a glint or specular area of the surface often comes from a small region of the surface, the effective size of projected reference point 300 is reduced, producing a three-dimensional image with improved lateral resolution. In one embodiment, regions of the surface that are likely to produce projected reference points 300 with small lateral extent are determined by scanning the beam and monitoring the return signal intensity while doing so. Areas producing bright returns are likely to be associated with glints or specular reflections. In another embodiment an autocorrelation is produced for the projected reference point alone by switching off light from path 305 with an optical switch. The autocorrelation of the projected reference indicates its extent in each direction and positions of projected reference point 300 may be chosen that produce an effectively small projected reference point 300. In another embodiment the three-dimensional image formed by projected reference point 300 is used as input or as a starting point for the reconstruction of the three-dimensional image from the autocorrelation as described below. In yet another embodiment, the separate measurement of the autocorrelation of the projected reference point is used to deconvolve the spread caused by the finite size of the reference point, thus improving the three-dimensional image.

In addition to the methods of creating a projected reference point as described above, it is also understood that projected reference points may be created by other methods of creating recognizable reference points including, but not limited to, utilizing multiple radiation sources.

Figure 3B:
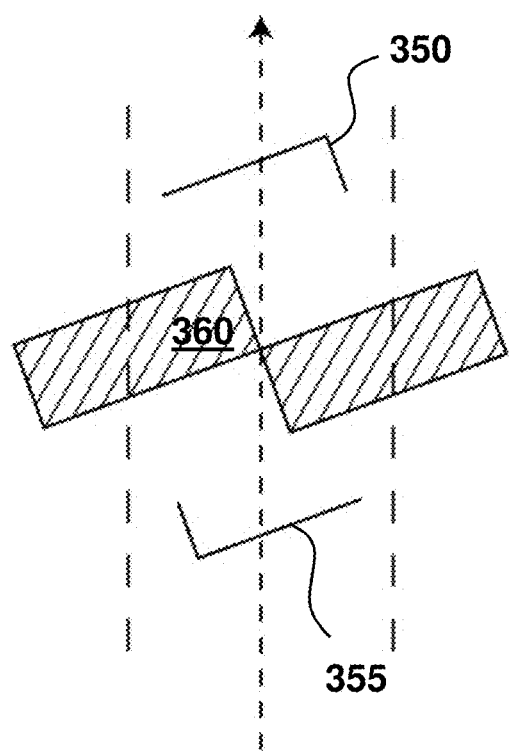
FIG. 3b shows an autocorrelation with an offset region of the autocorrelation being produced by a reference point.

Also with reference to FIG. 3b, in another embodiment of the invention, the sampling rate of the speckle pattern is reduced by a factor of approximately two in both the x and in the y directions so that aliasing in these directions, as indicated by dashed lines is allowed to occur in central autocorrelation 360. This aliasing does not affect copy 350 and inverted copy 355 so that fewer detector elements, by a factor of approximately two in both the x and the y directions of detector array 115, can be used to obtain the same resolution.

In reference to FIG. 4, in an additional embodiment of the invention, curved surface 400 produces a virtual reference point that is offset in range from region of interest 405 of object 105, thus forming copy 410 and inverted copy 415 that are sufficiently separated in range from central autocorrelation 420 and can be extracted from the autocorrelation by a regional image selection technique (indicated by the dashed box) to form a three-dimensional image of region of interest 405 without the need for reconstructing the image from the autocorrelation. In one embodiment of the invention, the curved surface is transparent and lies in front of region of interest 405, thus allowing the bulk of the light in illumination beam 108 to strike region of interest 405. In one embodiment curved surface 400 is the cornea of an eye. In one embodiment the region of interest 405 is an iris. In another embodiment, the region of interest includes the retina, floaters, or internal structures of the eye, such as the lens. In one embodiment a three-dimensional iris scan is produced for the purpose of recognizing and identifying people for control access. In another embodiment, the three-dimensional iris scan is used to recognize or categorize people at long ranges. In another embodiment of the invention the three-dimensional images of the eye are used for ophthalmological purposes.

Many other embodiments of the invention utilizing a curved surface 400 are anticipated. Additional embodiments of the curved surface include, but are not limited to, a curved component of a three-dimensional microscope, a lens, a transparent cover, and a cover glass on a specimen box. These additional embodiments have applicable uses for purposes such as, but not limited to, ophthalmology, biometric authentication, microscopy, remote imaging and other imaging purposes.

The systems and methods of this invention also provide for comparisons of autocorrelations. In one embodiment of the invention, the autocorrelation of object 105 is produced for two different viewing angles that have many scattering points on the surface in common. Different viewing angles may be obtained, for example, from relative rotations of object 105 with respect to illumination beam 108. The two autocorrelations are rotated such that points in the autocorrelation that are produced by points that are common to both views overlap. The two autocorrelations are then compared point by point. Regions that are supported in one autocorrelation and not the other are related to points that have become shadowed or have become visible due to the relative rotation of the object between measurements. These points may also arise from specular returns that are present for only one of the measurements. For example, if a bright point or specular reflection occurs in one measurement and not the other, then the difference between these two measurements provides an estimate of a dominant copy, which is taken as a three-dimensional image of the object. In some cases the three-dimensional image may consist of multiple dominant copies. In this case, reconstruction techniques disclosed below may be used to further refine the three-dimensional image.

In another embodiment of the invention, autocorrelations are produced for two similar objects 105 that are to be compared or for the same object to be compared at different times with the possibility of changes occurring over time. The autocorrelations to be compared are rotated so as to maximize the area of overlap and change detection between the two autocorrelations is implemented. The variations between autocorrelations are related to differences in physical features of the objects. Physical features, or partial representations, of an object produce their own contribution to the autocorrelation. It can be verified that a physical feature is not contained in an object if all the support points in the autocorrelation that correspond to the partial representation representing the feature are not contained in the autocorrelation of the object. Thus, presence or absence of features of objects in a scene can be sensed using the autocorrelation of the scene and knowledge of the autocorrelation of the physical features of interest.

Figure 5:
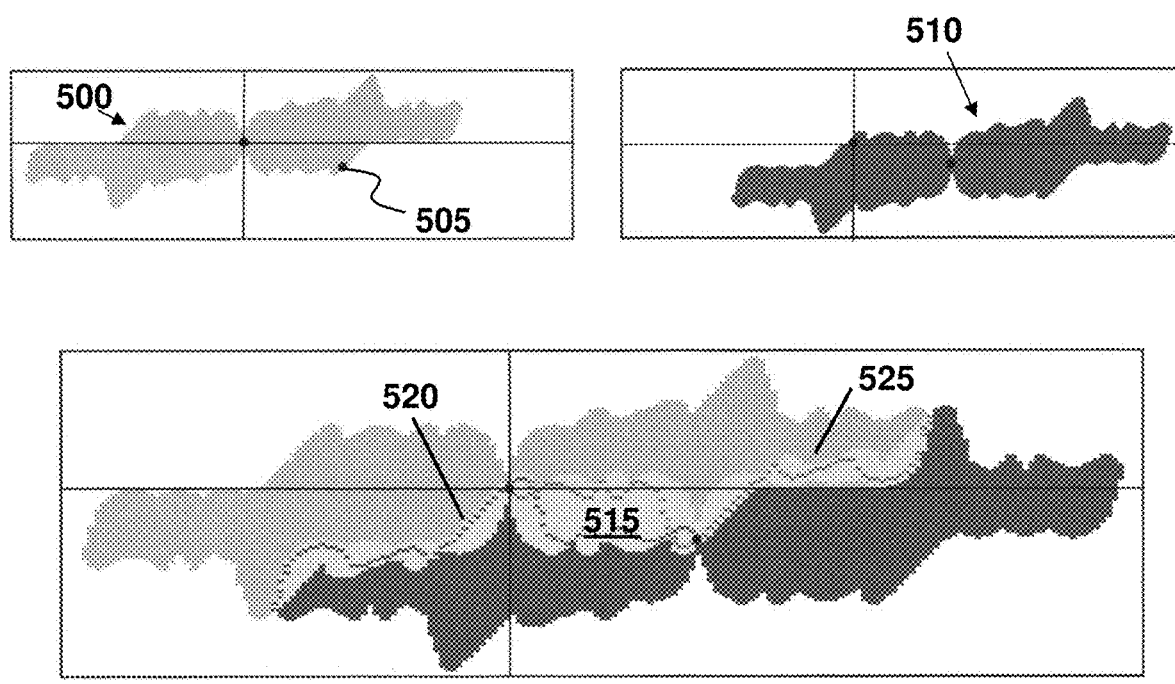
FIG. 5 shows the effect of a shift-and-compare operation on an autocorrelation.

Referring to FIG. 5, the concepts underlying one embodiment of systems and methods to shift-and-compare autocorrelations to construct a representation of an object can begin to be illustrated. In one embodiment of the invention, a three-dimensional image of object 105 is formed from the autocorrelation corresponding to that object by reconstructing an estimate of a copy or of an inverted copy from the autocorrelation. With reference to FIG. 5, for simplicity in explaining the concepts underlying the invention, the autocorrelation of a two-dimensional object is considered. These concepts generalize to higher dimensions so that it is sufficient to consider two dimensions in illustrating the concepts. Autocorrelation 500 is a two-dimensional autocorrelation with the vertical axis representing range and the horizontal axis representing a lateral dimension. Autocorrelation 500 contains a set of support points, one of which, point 505 is indicated in the drawing. Shifted autocorrelation 510 is formed by shifting autocorrelation 500 such that the origin of autocorrelation 500 lies on shift 505. Regions of overlap between the shifted and original autocorrelations are displayed in overlap region 515. It can be proven that for any shift point 505 which is a support point of autocorrelation 500, that the overlap region 515 contains an intact copy 520 and inverted copy 525. In this illustration, copy 520 corresponds to a face profile. The shift-and-compare process, is thus a powerful tool for eliminating points in the autocorrelation that do not lie on a copy and forming a reconstruction by successive shift-and-compare operations. As long as subsequent shifts lie on the copy being reconstructed, it is guaranteed in the noiseless case that only points lying on copies other than the one being reconstructed will be discarded by a sequence of shift-and-compare operations. Because every practical measurement has a noise floor, it is possible for some points in the autocorrelation to fall below the noise floor and to be clipped by a threshold function when estimating the support of the autocorrelation function. Therefore, it is advantageous in some situations to choose shifts corresponding to bright points on the copy and to truncate the process by not allowing points below a certain brightness to be used as shifts. The compare operation may take many forms. Three forms are described in the definitions section, giving rise to the terms shift-and-intersect, shift-and-min, and shift-and-rank. A series of shift-and-compare operations using good shifts tends to eliminate additional points not lying on the copy being reconstructed.

A shift-and-compare operation can be performed numerically in many ways. In one embodiment of the invention, the autocorrelation is treated as a three-dimensional array of numbers. In another embodiment, the size of the array that needs to be considered when comparing previous shifts is reduced on-the-fly as the process continues so as to be equal to the bounding box corresponding to the intersection of all prior shifted arrays, including the original array. Reducing the boundary box reduces the number of computations that must be performed when doing the comparison operation. In another embodiment of the invention, surviving points are listed sequentially including the coordinate positions and the brightness. As the process continues, this operation becomes more efficient because the length of the list decreases and fewer and fewer points need to be compared.

Figure 6:
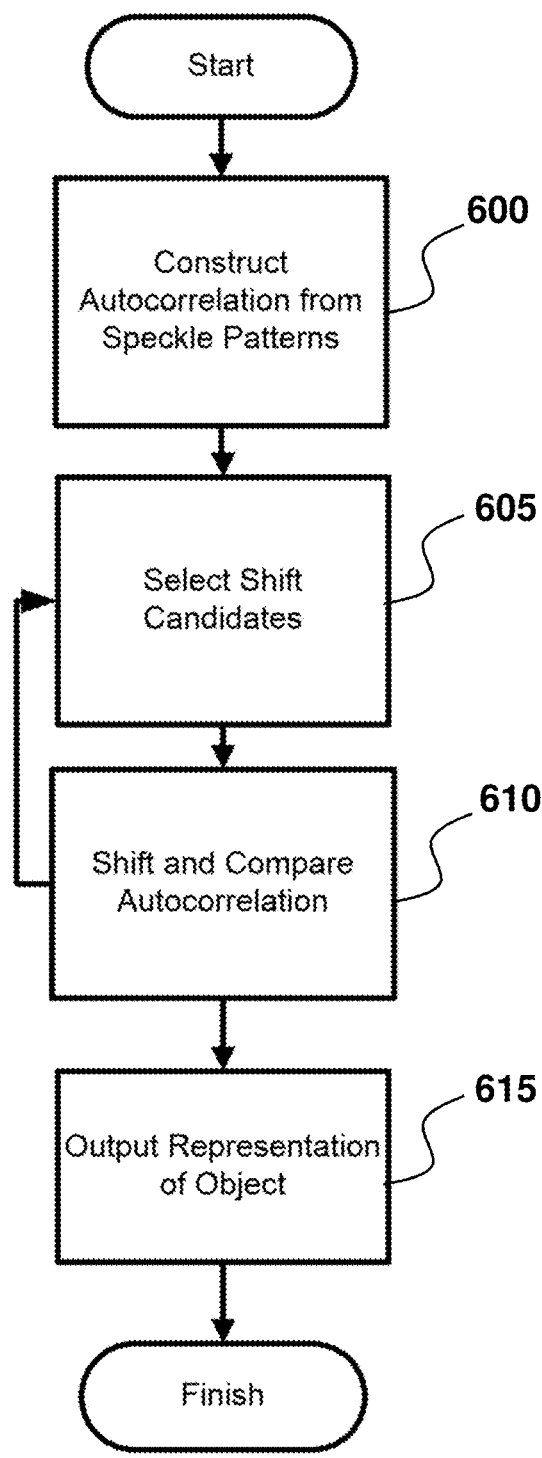
FIG. 6 shows a process flow diagram of one embodiment of the method to reconstruct an image from an autocorrelation.

The crux of the reconstruction problem is to determine a list of good shifts that is effective in eliminating unwanted points. FIG. 6 is a high-level flow chart describing the reconstruction process. The first step of the process 600 is to construct the autocorrelation from the speckle pattern intensity. The second step 605 is to select one or more good shift candidates. The third step 610 is to perform a shift-and-compare operation on the autocorrelation function using one or more good shifts, thus producing a partial reconstruction. The process then iterates between selecting shifts 605 and performing shift-and-compare operations 610. After the first shift, the shift-and-compare operation compares the shifted autocorrelation with the partial reconstruction formed by prior shifts. Once a set of shift-and-compare operations have been formed, the final step is to output a three-dimensional representation of the object 615.

Figure 7:
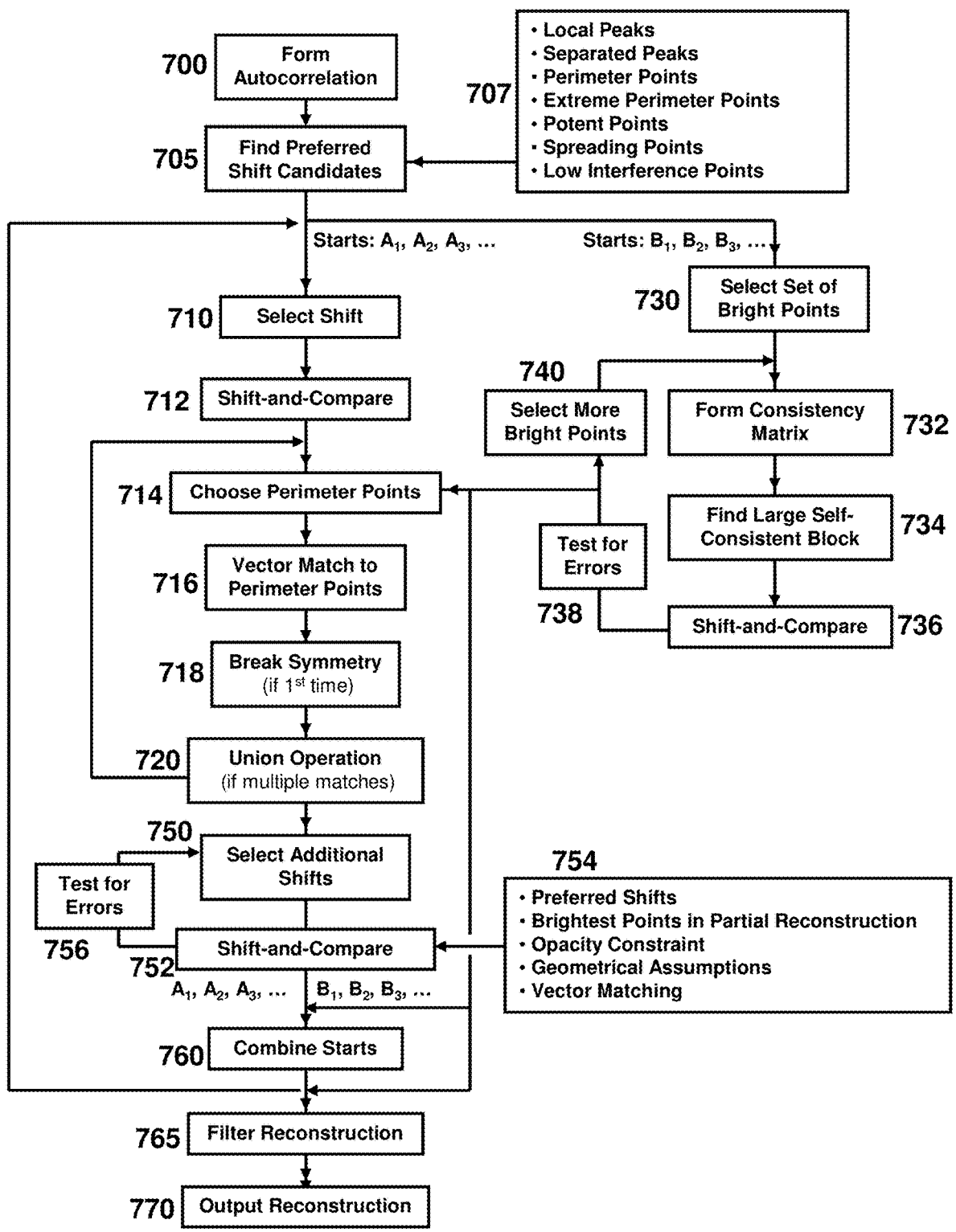
FIG. 7 shows a process flow diagram of one embodiment of the method to reconstruct an image from speckle patterns.

FIG. 7 is a lower-level flow chart showing additional details in the reconstruction process for one realization of the invention. The steps shown and the order that they are shown in is only one example of how the various processing tools and components illustrated as blocks in the flow chart can be put together to form a reconstruction. Many of the steps in the process may not be necessary and can be entirely skipped for many reconstruction problems. There are numerous paths through the flow chart, and entire blocks within the chart can be bypassed. FIG. 7 is meant to describe a set of tools and to illustrate how they can be used together to solve some of the most difficult reconstruction problems. Many typical reconstruction problems can be solved by using a small subset of the steps illustrated on the chart.

At a high level, FIG. 7 can be broken into six major sections. Initialization steps are described in blocks 700-707. Termination steps are described in blocks 765-770. A method for selecting a first shift and finding additional good shifts based on vector matching is described in blocks 710-720. Blocks 730-740 describe a method for selecting a set of shifts that are likely to lie on a bright copy and determining which of these shifts are self-consistent. It includes an error testing step to help guard against the possibility of introducing shifts that are not good shifts. Blocks 750-756 describe methods for selecting shift candidates that are likely to be good shifts. An error testing step may also be included here. Block 760 pertains to methods to combine different starts that may be produced by making different choices of the initial shift in block 710 or by starting with different sets of simultaneous shifts in block 730. For each of the three occurrences of shift-and-compare (blocks 712, 736, and 750) a choice can be made as to which compare operation to use. Common choices in order of computational difficulty are shift-and-intersect, shift-and-min, and shift-and-rank.

The individual blocks in FIG. 7 are now described in greater detail. The first step in the process, block 700, is to form an autocorrelation from a speckle measurement or to be given an autocorrelation as the starting point. Block 705 pertains to finding preferred shifts according to one or more of the selection criteria listed in block 707, including local peaks, separated peaks, perimeter points, extreme perimeter points, potent points, spreading points, and low interference points. This list of criteria is not exhaustive, but only provides examples of the type of selection rules that might be used. The objective of the selection rules is to provide first shift candidates that eliminate many points and are likely to lie on bright or dominant copies in the autocorrelation.

Figure 8:
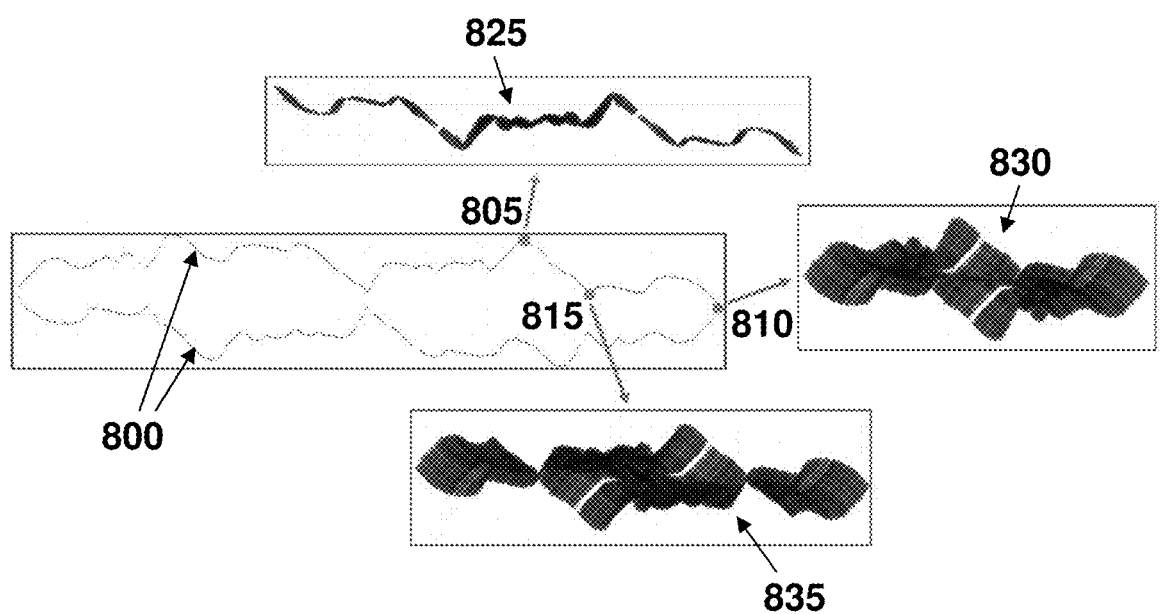
FIG. 8 shows a representative example of one embodiment of shift-and-compare methods in this invention.

In reference to FIG. 8, in another embodiment, first shifts are chosen from a list of potent points taken from perimeter points 800. Shift candidates 805, 810, and 815, which are taken from a list of perimeter points and extreme perimeter points are tested to form partial reconstructions 825, 830, and 835, respectively. The number of surviving points for each shift are calculated and displayed. Shift 805 produces by far the fewest number of survivors and is used as the initial shift in this embodiment.

Figure 9:
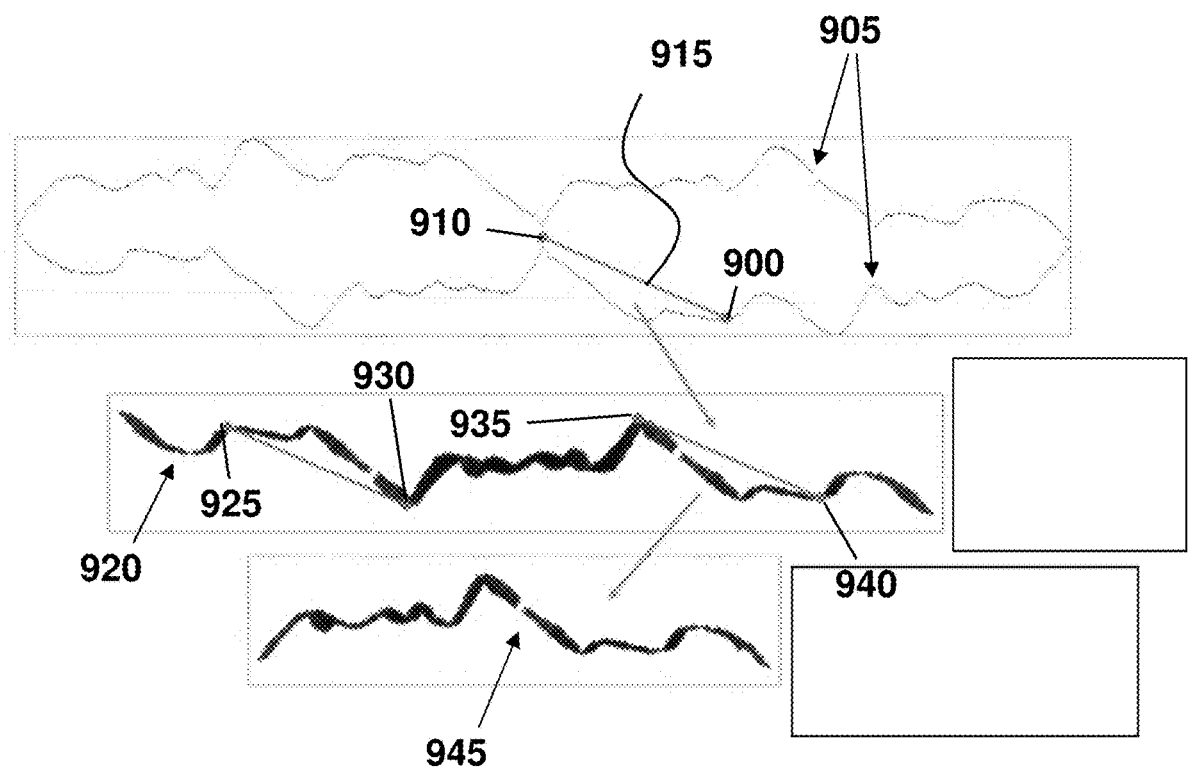
FIG. 9 illustrates a vector matching operation for determining additional shift candidates.

Different values of the first shift may produce different unique starts, labeled $A_1$, $A_2$, $A_3$, etc., that may be combined later in block 760 to provide a larger set of good shifts that will eliminate many more points from the autocorrelation than one start used alone. In block 710 a first shift is selected from the list of preferred shift candidates. In block 712, a shift-and-compare operation is performed using this shift. Next, in block 714, a perimeter point or extreme perimeter point is chosen from the list of preferred shift candidates. This perimeter point is then used in a vector matching operation 716 to determine a cluster of shift candidates. The process of vector matching is illustrated in FIG. 9. Support point 900 is taken from a set of perimeter points 905 and is selected to form the test vector 915. The ends of test vector 915 are the origin 910 and the support point 900. One point of vector 915 is placed on each point in partial reconstruction 920. Points are tagged in the partial reconstruction where both ends of the vector overlap with a support point of partial reconstruction 920. Point pair 925 and 930 and point pair 935 and 940 indicate positions where the vector ends align. In this case the vector only overlaps in two places. One of these overlaps corresponds to a fit to the copy and the other overlap corresponds to a fit to the inverted copy. Point pair 935 and 940 is chosen to break symmetry. In this example, running a shift-and-compare operation with points 935 and 940 as shifts almost entirely eliminates the other copy, leaving a partial reconstruction 945 with a greatly reduced number of points that closely resembles the object.

Returning to FIG. 7, in many cases, the vector fits into multiple places in a region of points, and if symmetry has not been broken, it is only guaranteed that two of these fits correspond to good shifts. In order to guarantee that a mistake is not made in the selection of shift candidates at this point, the entire cluster of shifts can be run using a union operation or a maximum operation on the individual shift candidates in the cluster of shifts. Since at least one of the shifts in the cluster of shifts is guaranteed to be a good shift, performing the union operation or the maximum operation on this combination of shifts guarantees that no points on the copy are eliminated. If vector matching produces a cluster with more than two vector matches after the first shift, then one has the option to apply the entire set as a union operation and keep both the copy and inverted copy in tact, or to break the symmetry at this point. The symmetry of having two copies surviving may aid in the selection of good shifts. In the embodiment illustrated in FIG. 7, symmetry is broken at this point. In one embodiment, symmetry is broken by dividing the pairs of shift candidates in the cluster of shifts into two halves such that one half is point symmetric about the origin with respect to the other half. In this dividing process, point pairs corresponding to a given vector match are kept together as a unit. Because of the symmetry of the resulting two sets of shift candidates, each group is guaranteed to contain at least one good shift. Thus, symmetry may be broken without making an error. After the union operation 720 is completed, there is a choice as to iterate the procedure using a new perimeter vector or to drop down to block 750 and select an additional shift using one or more of the constraints in block 754. Typically, since the process of vector shifting 716 and performing a union operation 720 is guaranteed not to produce a mistake, it is preferred to iterate this loop. If stagnation occurs, then further progress can likely be made by dropping down to block 750.

In block 750, additional shifts are selected according to one or more of the rules for selecting addition shift candidates listed in block 754. The list in block 754 is not exhaustive, but merely illustrates the type of rules that might be employed in the selection process. The listed rules include selecting new shifts from the partial reconstruction that are also in the preferred candidate list 707, selecting bright points in the partial reconstruction, or selecting points based on the opacity constraint, geometrical assumptions, or vector matching. A shift-and-compare operation 750 is then performed using a new shift, and the option exists to test for errors 756 at various stages of the iteration. It is not necessary to test during every loop of the iteration. If an error has been made, then it will eventually become obvious in terms of too many points being eliminated so that a simple test will suffice. In order to minimize time, there should be a proper balance between the time spent testing and the time spent exploring paths. If an error has been made, then the process can be picked up at a prior point where it is believed that no errors have been made.

Figure 10:
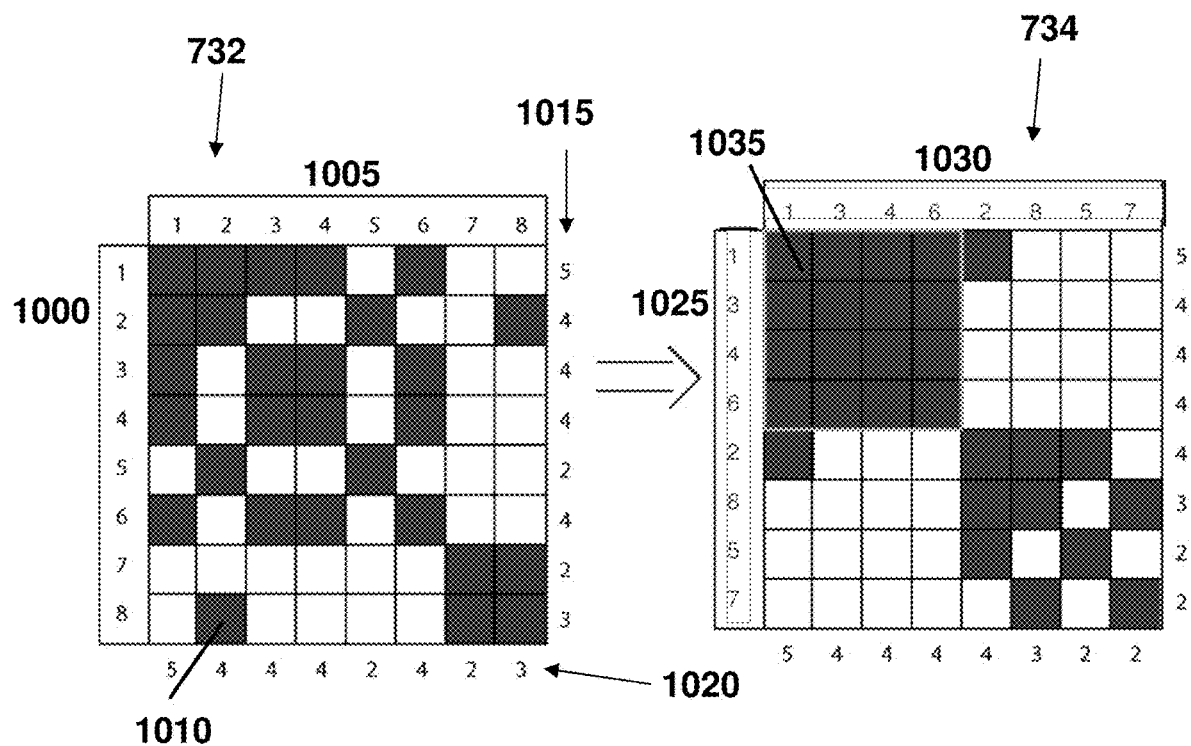
FIG. 10 shows a representation of one embodiment of a consistency matrix and reordering of the consistency matrix.

Now, the branch of the flow chart is explained that begins with block 730. This branch relates to the possibility of creating additional new starts labeled $B_1$, $B_2$, $B_3$, . . . . The first step in this branch, selecting a set of bright points 730, refers to selecting points from the list of preferred shift candidates that are likely to lie on one of the brightest copies. For low interference events, which are more likely to occur for points not too close to the origin, the brightest copies tend to produce separated peaks, i.e., local peaks in the autocorrelation that are larger than nearest neighbors within a given radius. In one embodiment of the invention, block 730 is implemented by making a list of the brightest of these separated peaks. FIG. 10 illustrates the process of forming a consistency matrix 732 and reordering the consistency matrix to produce a large block of self-consistent points 734. The row headings 1000 and column headings 1005 of consistency matrix 732 refer to indices that represent an initial ordering of the points for which the matrix is generated. Black elements 1010 of consistency matrix 732 indicate point pairs that are self-consistent, the indices of the point pairs corresponding to row headings 1000 and column headings 1005. In one embodiment, the initial step in reordering the elements of the matrix is to count the number of times each point is self-consistent with a point in the list. These numbers are indicated by row summation 1015 and column summation 1020. In reordered consistency matrix 734, the row headings 1025 and column headings 1030 have been reordered according to the ranking of the row summation 1015 (or column summation 1020). The row headings 1025 (or column headings 1030) in the resulting contiguous block 1035 refer to the indices of the set of self-consistent points used in shift-and-compare operation 736.

In one embodiment reordering is achieved by counting the number of points in the list each point is self-consistent with. The rows and columns of the matrix are then reordered to place those that are consistent with more points at the top of the list. In an additional step, the points are reordered to produce a large, preferably the largest possible, contiguous block in the top left corner of the matrix. The points corresponding to this contiguous list are then all self-consistent and are likely to lie on a copy. These shifts can be run in parallel in shift-and-compare operation 736, and tested for errors 738. More bright points are then selected from the intersection of the partial reconstruction and other preferred points that are likely to lie on the copy. It is possible that shifts creep into the list that, although being self-consistent with the other shifts, do not lie on a copy and are not self-consistent with other points on the copy. Therefore, in order to maximize the size of the self-consistent list, it may be necessary to allow points to be removed to test whether a larger self-consistent list could be formed in the absence of these points. The consistency matrix approach may generate an adequate reconstruction without being tied into the other branches of the flow chart. In this case the process flow goes directly to the filter reconstruction block 765, assuming the reconstruction has extra points in a column to be removed by the range filtering process. Assuming that different starts have been generated and none of the starts produced a satisfactory reconstruction by itself, the starts can be combined into a larger start in block 760. As part of the process of combining starts, a shift-and-compare operation is performed to produce a partial reconstruction that is smaller than the partial reconstruction obtained by the individual starts. If the partial reconstruction produced by combining starts is satisfactory, then the process goes to block 765. If it is not, the process returns to block 710 or block 730 for more iterations.

If more than one start has been generated, these starts may be combined into a single start in block 760. The offset necessary for combining starts is determined by a process known as cross-matching. Since multiple starts can be combined sequentially one at a time, it is sufficient to describe the process of combining two starts. Considering a first and a second start, the process is performed by first matching the first start with the second partial reconstruction. Matching is achieved by selecting a point from the first start to serve as an indicator point for defining the relative position of that start. Matches between the first start and the second partial reconstruction are then determined by translating the indicator point on the first start such that it lies sequentially on each point in the second reconstruction. A match occurs if every point in the first start overlaps with a support point of the second partial reconstruction. (This description in terms of choosing an indicator point and setting the point on a support point in the partial reconstruction is only meant to be a description of the logic for one embodiment of the invention. The invention anticipates the use of algorithms such as, but not limited to the cross-correlation algorithm implemented through the use of FFTs, that perform these types of operations in parallel.) If the first start overlaps with the second partial reconstruction in only one place, then the offset must be correct and the points on the second partial reconstruction where this overlap with the first start occurs are added to the second start to produce a combined start with more elements. A new partial reconstruction with fewer elements can then be formed by performing a shift-and-compare operation using all the points in the combined start as shifts. If the first start overlaps with the second partial reconstruction in more than one location, then the combination of all of the points in the second partial reconstruction where these overlaps occur forms a cluster of shift candidates. There is now the option of running a union operation, or a maximum operation, on this cluster of shift candidates to produce a new partial reconstruction with fewer points.

In a second optional step of the cross-matching operation, the above procedure is repeated with the second start being matched to the first partial reconstruction. Again, if a match occurs at only one location, then the points in the first partial reconstruction that overlap with the second shifted start are added to the first start to produce a combined start with more elements. A new partial reconstruction with fewer elements can then be formed by performing a shift-and-compare operation using all the points in the combined start as shifts. Again, if the second start overlaps with the first partial reconstruction in more than one location the combination of all of the points in the second partial reconstruction where these overlaps occur forms a cluster of shift candidates. Once again, there is the option of running a union operation, or a maximum operation, on this cluster of shift candidates to produce a new partial reconstruction with fewer points.

A further step in the process of cross-matching to combine starts is to compare the list of offsets of the first start that produces a complete overlap with support points of the second partial reconstruction with the list of offsets of the second start that produces a complete overlap with support points of the first partial reconstruction. Since the true offset that produces a combined start depends on which start is being used as the base in the comparison, and since the magnitude of the offset must be the same in both cases for the offset that correctly combines the two starts, a reduced list of potential offsets can be obtained by switching the sign of the coordinates of the offsets for one of the two lists and forming the intersection. The correct offset for combining the two lists must be contained in the intersection of these two lists. If the intersection contains only one offset, then this offset must be the correct offset. Thus, the two starts can be combined into a new start with more elements. The sign of the offset should be chosen that produces the brighter copy. If the intersection contains more than one offset, then each of these offsets can be applied to produce a cluster of shift candidates. A partial reconstruction with fewer elements can then be formed by performing a union operation or a maximum operation on the cluster of shift candidates.

A final optional step that can be formed on starts or combined starts is to translate the start so that it falls on the brightest copy. This can be accomplished by performing a three-dimensional cross-correlation. The location of the maximum point in the cross-correlation indicates the offset that is likely to translate the start to the brightest copy. The same technique can be used to translate a partial reconstruction to the brightest copy once the number of extra points in the partial reconstruction has been sufficiently reduced.

A final optional step in the reconstruction process is to filter the reconstruction in range 765 to eliminate residual multiple values in range. If a bright copy is being reconstructed, a very effective means of eliminating residual range points is to keep the brightest point in each column. Other examples of effective means for smoothing in range are to form the center of mass of the residual points in a column, to take the median point, and to smooth by taking into account the position of residual points in neighboring columns.

It will be appreciated that the processes and methods disclosed herein may be realized in hardware, software, or any combination of these suitable for the 3D imaging and reconstruction techniques described herein. This includes realization in one or more microprocessors, microcontrollers, embedded microcontrollers, programmable digital signal processors or other programmable device, along with internal and/or external memory. This may also, or instead, include one or more application specific integrated circuits, programmable gate arrays, programmable array logic components, or any other device or devices that may be configured to process electronic signals. It will further be appreciated that a realization may include computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as a radiation source, a sensor and/or computer in a number of ways or all of the functionality may be integrated into a dedicated, standalone image capture device. All such permutations and combinations are intended to fall within the scope of the present disclosure.

It will also be appreciated that means for performing the steps associated with the processes described above may include any suitable components of the imaging apparatus described above, along with any software and/or hardware suitable for controlling operation of same.

While the invention has been disclosed in connection with certain preferred embodiments, other embodiments will be recognized by those of ordinary skill in the art, and all such variations, modifications, and substitutions are intended to fall within the scope of this disclosure. Thus, the invention is to be understood with reference to the following claims, which are to be interpreted in the broadest sense allowable by law.

What is claimed is:

1. An imaging apparatus comprising:
a first source of radiation configured to create a first beam of radiation having a wavelength and illuminate an object to produce a projected reference spot at a first location on the object;
a second source of radiation configured to create a second beam of radiation that is mutually coherent with the first beam of radiation and simultaneously illuminate the object to produce a wider-area illumination beam at a second location on the object;

the second beam of radiation having the wavelength of the first beam of radiation;

a controller configured to control the wavelength of the first beam of radiation and the second beam of radiation;

the controller configured to create at least two instances of the wavelength;

at least one sensor at a location relative to the object configured to determine at least one speckle pattern intensity for the at least two instances of the wavelength;

a processor configured to receive information from the at least one sensor; and the processor configured to utilize the projected reference spot and the at least two instances of the wavelength to produce a three-dimensional representation of a region of the second location on the object.

2. The imaging apparatus of claim 1 wherein the second source of radiation is the same as the first source of radiation and further comprising a beam splitter configured to produce the first beam of radiation and the second beam of radiation from the first source of radiation.

3. The imaging apparatus of claim 2 wherein the first source of radiation is a tunable laser.

4. The imaging apparatus of claim 1 wherein the projected reference spot is a focused beam of radiation.

5. The imaging apparatus of claim 1 wherein the first location on the object and the second location on the object overlap.

6. The imaging apparatus of claim 1 further comprising a means for moving the first location on the object with respect to the second location on the object.

7. The imaging apparatus of claim 1 wherein the controller is further configured to control an optical path delay between the first beam of radiation and the second beam of radiation.

8. The imaging apparatus of claim 7 wherein the optical path delay is controlled by an optical fiber length.

9. The imaging apparatus of claim 1 wherein the processor further comprises means for constructing at least one autocorrelation and executing a regional image selection technique to construct the three-dimensional representation of the region of the second location on the object.

10. A method for constructing a three-dimensional image of an object comprising the steps of:

outputting a first beam of radiation having a wavelength and illuminating an object to produce a projected reference spot at a first location on the object;

outputting a second beam of radiation that is mutually coherent with the first beam of radiation and simultaneously illuminating the object to produce a wider-area illumination beam at a second location on the object;

changing the wavelength;

determining at least one speckle pattern intensity for at least two wavelengths with at least one sensor;

receiving information from the at least one sensor;

utilizing the projected reference spot and at least two instances of the wavelength to produce a three-dimensional representation of a portion of the second location on the object.

11. The method of claim 10 further comprising:

splitting a beam from a coherent source of radiation to produce the first beam of radiation and the second beam of radiation.

12. The method of claim 11 wherein the splitting the beam from the coherent source of radiation comprises splitting the beam from a tunable laser.

13. The method of claim 10 further comprising focusing the first beam of radiation on the first location on the object to form the projected reference spot.

14. The method of claim 10 further comprising overlapping the first location on the object and the second location on the object.

15. The method of claim 10 further comprising moving the first location on the object with respect to the second location on the object.

16. The method of claim 10 further comprising controlling an optical path delay between the first beam of radiation and the second beam of radiation.

17. The method of claim 16 wherein the controlling the optical path delay further comprises controlling an optical fiber length.

18. The method of claim 10 wherein the utilizing the projected reference spot and at least two instances of the wavelength to produce a three-dimensional representation of a portion of the second location on the object comprises constructing at least one autocorrelation and executing a regional image selection technique.

19. A method for constructing a three-dimensional image of an object comprising the steps of:

splitting a laser beam having a wavelength to form a first beam of radiation and a second beam of radiation;

the first beam of radiation illuminating an object to produce a projected reference spot at a first location on the object;

the second beam of radiation illuminating the object to produce a wider-area illumination beam at a second location on the object;

the first beam of radiation and the second beam of radiation simultaneously illuminating the object;

controlling an optical path delay between the first beam of radiation and the second beam of radiation;

controlling the wavelength;

determining at least one speckle pattern intensity for at least two instances of the wavelength with at least one sensor;

receiving information from the at least one sensor;

utilizing the projected reference spot and the at least two instances of the wavelength and the optical path delay to produce a three-dimensional representation of a region of the object illuminated by the second beam of radiation.

20. The method of claim 19 further comprising overlapping the reference spot and the wider-area illumination beam on a surface of the object.

* * * * *